US009862757B2

United States Patent
Hu et al.

(10) Patent No.: US 9,862,757 B2
(45) Date of Patent: Jan. 9, 2018

(54) INHIBITOR TARGETING SPECIFIC COMPLEMENT SYSTEM, AND PREPARATION METHOD AND USE THEREOF

(71) Applicant: FUDAN UNIVERSITY SHANGHAI CANCER CENTER, Shanghai (CN)

(72) Inventors: Weiguo Hu, Shanghai (CN); Qian Qiao, Shanghai (CN); Xin Zhang, Shanghai (CN)

(73) Assignee: FUDAN UNIVERSITY SHANGHAI CANCER CENTER (CN)

( * ) Notice: Subject to any disclaimer, the term of this patent is extended or adjusted under 35 U.S.C. 154(b) by 6 days.

(21) Appl. No.: 14/916,800

(22) PCT Filed: Jul. 3, 2014

(86) PCT No.: PCT/CN2014/000638
§ 371 (c)(1),
(2) Date: Mar. 4, 2016

(87) PCT Pub. No.: WO2015/032167
PCT Pub. Date: Mar. 12, 2015

(65) Prior Publication Data
US 2016/0326231 A1 Nov. 10, 2016

(30) Foreign Application Priority Data

Sep. 5, 2013 (CN) .......................... 2013 1 0400969
Mar. 25, 2014 (CN) .......................... 2014 1 0114646

(51) Int. Cl.
| | | |
|---|---|---|
| A61K 38/00 | (2006.01) |
| C07K 14/705 | (2006.01) |
| A61K 38/17 | (2006.01) |
| A61K 45/06 | (2006.01) |
| C07K 14/47 | (2006.01) |

(52) U.S. Cl.
CPC ...... C07K 14/70596 (2013.01); A61K 38/177 (2013.01); A61K 38/1709 (2013.01); A61K 45/06 (2013.01); C07K 14/70503 (2013.01); *A61K 38/00* (2013.01); *C07K 14/4703* (2013.01); *C07K 2319/00* (2013.01)

(58) Field of Classification Search
CPC .. A61K 38/00; A61K 38/1709; A61K 38/177; A61K 45/06; C07K 14/4703; C07K 14/70503; C07K 14/70596; C07K 2319/00
See application file for complete search history.

(56) References Cited

U.S. PATENT DOCUMENTS

| | | | | |
|---|---|---|---|---|
| 7,930,109 B2 * | 4/2011 | Hass | .................... | C07K 14/745 435/183 |
| 2010/0150908 A1 | 6/2010 | Sidhu et al. | | |
| 2012/0189626 A1 | 7/2012 | Ashkenazi et al. | | |

FOREIGN PATENT DOCUMENTS

| | | |
|---|---|---|
| CN | 101107005 | 1/2008 |
| CN | 102015763 | 4/2011 |

OTHER PUBLICATIONS

Helmy et al. CRIg: A Macrophage Complement Receptor Required for Phagocytosis of Circulating Pathogens. Cell, 2006. vol. 124, pp. 915-927.*
Ruseva et al. Targeting sites of complement activation by engineering selective drug delivery. Abstracts. Molecular Immunology, 2009. vol. 46, pp. 2818-2871.*
Smith. Creative Expression: Mammalian Expression Vectors and Systems. The Scientist, 1998. pages 1-5. Accessed online on May 2, 2017 at http://www.the-scientist.com/?articles.view/articleNo/ 18796/title/Creative-Expression--Mammalian-Expression-Vectors-and-Systems/.*
Ruseva et al. An anticomplement agent that homes to the damaged brain and promotes recovery after traumatic brain injury in mice. PNAS, 2015. vol. 112, No. 6, pp. 14319-14324.*
Schumann et al. Production of recombinant proteins in *Escherichia coli*. Genetics and Molecular Biology, 2004. vol. 27, No. 3, pp. 442-453.*
International Search Report dated Sep. 26, 2014 corresponding with International patent application No. PCT/CN2014/000638.

* cited by examiner

*Primary Examiner* — Marcela M Cordero Garcia
(74) *Attorney, Agent, or Firm* — Ostrolenk Faber LLP

(57) ABSTRACT

An inhibitor targeting specific complement, the inhibitor targeting specific complement is a protein, the protein has a targeted inhibition function on the complement activation, and the amino acid sequence of the protein comprises CRIg extracellular domain and complement inhibiting domain; the amino acid sequence of the protein is consist of the CRIg extracellular domain and the complement inhibiting domain connected directly, or indirectly through a linker which can connect the two domains. The preparation method of the inhibitor targeting specific complement comprises connecting the protein polypeptides of the CRIg extracellular domain and the complement inhibiting domain by gene engineering technology. The protein can be used to prepare a drug targeting inhibition of complement activation. The inhibitor targeting specific complement, its preparation method and applications provided by the present invention, can be used in the treatment and prevention of human diseases caused by complement activation disorders. It has great potential application value and development prospects.

19 Claims, 8 Drawing Sheets

INHIBITOR TARGETING SPECIFIC COMPLEMENT SYSTEM, AND PREPARATION METHOD AND USE THEREOF

CROSS REFERENCE TO RELATED APPLICATIONS

The present application is a 35 U.S.C. §371 National Phase conversion of PCT/CN2014/000638, filed Jul. 3, 2014, which claims benefit of Chinese Application No. 201310400969.3, filed Sep. 5, 2013 and of Chinese Application No. 201410114646.2, filed Mar. 25, 2014, the disclosures of which are incorporated herein by reference. The PCT International Application was published in the Chinese language.

TECHNICAL FIELD

The present invention relates to a complement inhibitor in the field of biotechnology and pharmacy, and its development and applications, in particular, relates to an inhibitor targeting specific complement, and preparation method and use thereof.

BACKGROUND ART

Complement system is the main component of innate immunity; it's also an important modulator of adaptive immunity, which plays an important role in immune surveillance. It can not only remove the pathogenic bacteria and host cell debris invaded, but also coordinate the entire immunological and inflammatory process. The complement system can be activated by three ways: the classical pathway (CP), the alternative pathway (AP) and the lectin pathway (LP), it plays physiological function mainly through the products formed after the activation. The pathways include that the C3b/iC3b deposited on the membrane surface of the cells being attacked, recruiting immune effectors' cells such as mononuclear cells to eliminates the target cells by phagocytosis; anaphylatoxins such as C3a/C4a/C5a cause local inflammation; and the membrane attack complex (Membrane Attack Complex, MAC, that is C5b-9n) assembles poles on the surface of the target cell membrane and ultimately leading to cell lysis and death.

In order to prevent the "by-stander injury" effects of complement activation to the normal host cells in the process, the host has evolved more than 10 regulatory proteins, including circulatory C1-INH (C1 inhibitor), C4BP (C4 binding protein), factor I, factor H, S-protein, clusterin, and membrane-bound protein CD35/CR1, CD46/MCP, CD55/DAF, CD59 expressed on the surface of the cell membrane, and another complement membrane regulatory protein CRIg found in the near future.

CRIg was initially identified as C3b/iC3b receptor expressed on the surface of liver macrophage (Kupffer's cell). Through CRIg binding to C3b/iC3b, Kupffer's cells can phagocytize pathogen or other particles. The result of crystal structure study demonstrated that through specific binding to C3b/iC3b and subsequent inhibition of C3 convertase, CRIg can inhibit complement activation via alternative pathway at the early stage with a lower efficacy in compared with the canonical complement inhibitor on alternative pathway, factor H. Until now, there is no any report to develop the targeted complement inhibitor by utilizing the unique feature of CRIg binding to C3b/iC3b.

The versatile functions of the complement system are able to be finely tuned to establish a delicate balance between activation and inhibition but the tipping of this delicate balance has been attributed to initiation, progression and treatment of various human disorders.

Numerous studies have demonstrated that the excessive complement activation contributes, at varying degree, to the occurrence and progression of various human diseases, such as autoimmune hemolytic anemia, autoimmune thrombocytopenia, aplastic anemia, systemic lupus erythematosus, rheumatoid arthritis, ankylosing spondylitis, atherosclerosis, Parkinson's disease, Alzheimer's disease (senile dementia), asthma, allergy, psoriasis, myasthenia Gravis, multiple emitting hardening, clone's bowel disease. Therefore, the drug research and development of complement as the therapeutic target, including inhibitors of complement system renewed attention. The complement system inhibitors, especially the complement-targeted therapeutics holds great potential with social and economic value.

After decades of investigation for the research and development of complement targeting inhibitor, including the protein Compastatin combined with C3 and the recombinant monoclonal antibody Eculizumab against C5 (Soliris, Alexion Pharmaceuticals), both have some obvious deficiencies. Compastatin has entered the pre-clinical trials, however, it inhibits C3 function of all parts thus leads to a potential risk of infection.

Eculizumab has been used for the treatment of paroxysmal nocturnal hemoglobinuria (PNH), but its intellectual property ownership belongs to foreign countries and it has an extremely high price, with a single year of treatment costing $409,500. The annual sales of Soliris in 2009 and 2010 are $ 2.95 and 5.41 billion US dollar.

PNH is an acquired hemorrhagic disease due to PIG-A mutation, thus resulting in the absence of two glycosylphosphatidylinositol (GPI)-anchored complement membrane regulatory proteins CD55 and CD59 on blood cell membrane. Therefore, the PNH blood cells are very susceptible to complement attack, and prone to infection caused by leukocyte decrease, hemolysis caused by hemocytocatheresis, and platelet activation. It eventually leads to repeated infection, haemolytical, thrombosis, renal failure, bone marrow failure and the lung moves venous pressure rise and other disease. These diseases getting worse progressively are no cure before the occurrence of Eculizumab monoclonal antibody, which seriously threaten the patients' life. The mechanism of Eculizumab is through binding to C5 and inhibiting complement activation at the end of the complement cascade, subsequently blocking MAC deposition on the membrane of blood cells and the lysis of blood cells especially red blood cells, the Eculizumab has a good effect in clinical treatment of patients with PNH, and can significantly reduce thrombosis. With a single year of treatment, 66% PNH patients can stop blood transfusion.

However, the PNH patient's condition is still not complete remission after the application of Eculizumab monoclonal antibody theoretically, because the level of C3 complement cascade activation persists, and leads to the generation of C3b/iC3b and their deposition on the surface of blood cells, making these blood cells consumed by mononuclear cells phagocytosis, eventually leading to the extravascular hemolysis. This is also the reason that Eculizumab treatment is not very satisfactory. Therefore, to prevent the activation of complement on the C3 level in the early activation of complement instead of the C5 level at the end of Eculizumab, can significantly reduce both the MAC mediated intravascular hemolysis and C3b/iC3b mediated extravascular hemolysis, thus get better therapy efficiency.

DISCLOSURE OF THE INVENTION

The purpose of the present invention is to provide a complement system inhibitor, its preparation method and use in the preparation of a drug inhibiting the complement activation, the type of drug can achieve the effect of targeting inhibition to the complement activation and can be used in treatment and prevention of abnormal activation complement-mediated diseases.

To achieve the above purpose, the present invention provides an inhibitor targeting specific complement, wherein, the inhibitor targeting specific complement is a protein, the protein has a targeted inhibition function on the complement activation, and the amino acid sequence of the protein comprises CRIg extracellular domain and complement inhibiting domain; the amino acid sequence of the said protein is consist by the CRIg extracellular domain and the complement inhibiting domain connected directly, or indirectly through a linker which can connect the two domains;

The said complement inhibiting domain could be any one or several kinds from the combination of factor H, C1 inhibiting protein, C4 binding protein, factor I, S protein, clusterin, complement membrane regulatory protein CD35/CR1, CD46/MCP, CD55/DAF, CD59 or full-length or functional fragment of CRIg itself;

The linker is preferably the flexible linked peptide segment, but other linkers may also work.

The amino acid sequence of the protein is shown such as SEQ ID NO 2 or SEQ ID NO 4.

The present invention also provides a nucleic acid, wherein, the nucleic acid sequence encodes the said protein.

The base sequence of the nucleic acid is shown as SEQ ID NO 1 or SEQ ID NO 3.

The present invention also provides a vector, wherein, the vector contains the said nucleic acid.

The present invention also provides a preparation method of the inhibitor targeting specific complement, wherein, the method comprises the connecting of the protein polypeptides of the CRIg extracellular domain and the complement inhibiting domain by gene engineering technology;

The amino acid sequence of the said CRIg extracellular domain is shown as SEQ ID NO 10;

The said complement inhibiting domain could be any one or several kinds from the combination of factor H, C1 inhibiting protein, C4 binding protein, factor I, S protein, clusterin, complement membrane regulatory protein CD35/CR1, CD46/MCP, CD55/DAF, CD59 or full-length or functional fragment of CRIg itself;

The said gene engineering technology comprises:

Connecting the nucleic acid sequence encoding the CRIg extracellular domain and the nucleic acid sequence encoding the complement inhibiting domain directly or indirectly through the nucleic acid sequence encoding the flexible linked peptide segment by gene splicing overlap extension PCR (SOE PCR), then inserting the fusion sequence into eukaryotic expression vector, inducing the protein expression of the inhibitor targeting specific complement through eucaryotic protein expression system, and then finally purifying the resulting protein.

Protein expression system is consist by the host system, exogenous gene, vector and the like, which can realize the expression of the exogenous gene in the host. The host is the organism to express the protein, which can be bacterial, yeast, plant cell, animal cell, etc. Different sources are suitable for different proteins expression due to different characteristics of various organisms. The species of the vectors is conformed to the host. According to the different host, the vectors can be divided into prokaryotic (bacterial) expression vectors, yeast expression vectors, plant expression vectors, mammalian expression vectors, insect expression vectors and so on. Vectors contain exogenous gene fragment, which can be expressed in the host through the meditation of vector.

The present invention also provides an application of the inhibitor targeting specific complement in the preparation of a drug targeting inhibition of the complement activation.

The present invention also provides an application of the inhibitor targeting specific complement in the preparation of drug for protecting the blood cells in patients with paroxysmal nocturnal hemoglobinuria and the cells attacked by complement of other diseases, such as membranoproliferative glomerulonephritis, atypical soluble hemorrhagic uremic syndrome and age-related macular degeneration from complement attack.

The present invention also provides for a drug, wherein, the active ingredient of the said drug is the protein used as inhibitor targeting specific complement. The drug chose the protein purified and obtained from the secretory expression in eukaryotic systems, in vivo and in vitro experiment confirmed that it has the targeted complement inhibiting function and good drug binding properties. The drug was demonstrated in vitro experiments using PNH patients, in which the drug showed a IC50 less than 100 nM. It was showed in vivo experiments the mesangioproliferative glomerulonephritis of rat was significantly attenuated by the drug treatment.

The pharmaceutical dosage form of the drug is preferably for injection. Other dosage forms can also be used, such as external coating, and the like.

The mode of administration of the drug includes:

(1) direct administration.

(2) through vector system that can carry or express the drug administration.

Compared with the prior art, the present invention has the following advantages and technical effect:

The present invention connect CRIg which has targeting action after binding with the fragment C3b and/or iC3b from the activation of the complement component C3, and another component with the complement inhibiting effect, such as Factor H directly or indirectly through a flexible peptide segment (Gly4Ser) 3 and so on to prepared a fusion protein through the genetic engineering method and finally achieve the effect of targeted inhibiting complement activation.

The present invention is a novel targeted complement inhibitor, which can specifically target to the activation site of complement in vivo, and long-term inhibit complement activation and the cell and tissue damages mediated by complement activation. Therefore, the target complement inhibitors provided by the present invention has great potential for medicinal application value and development prospects. This type of drugs can be used in treatment and prevention of various human diseases related to complement abnormal activation.

DESCRIPTION OF THE PREFERRED EMBODIMENTS

Figure 1:
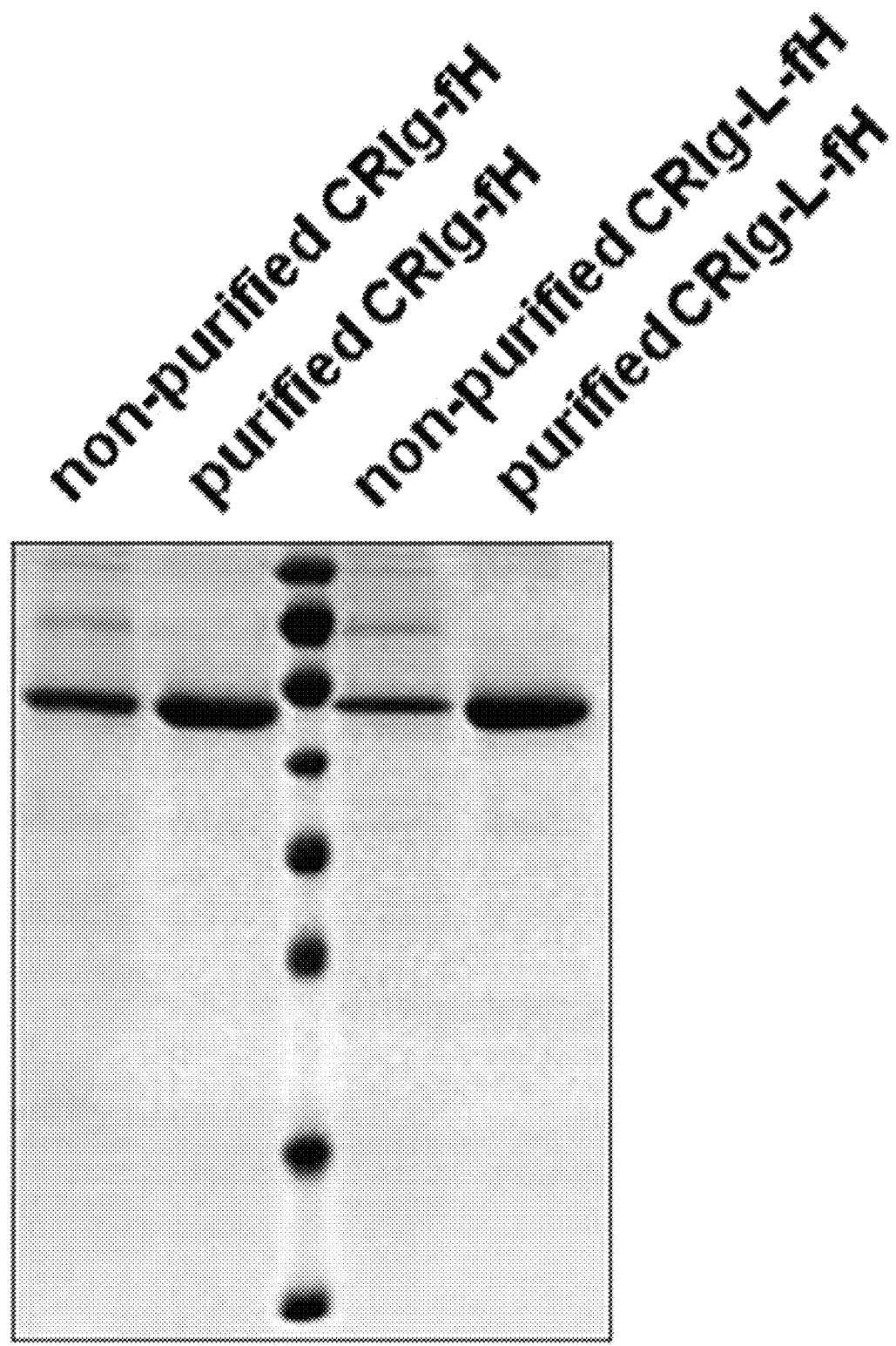
FIG. 1 is shown the expression and purification of CRIg-fH and CRIg-L-fH.

The following illustration with figures will make a further description to the embodiments of this present invention.

The present invention provides an inhibitor targeting specific complement, wherein the inhibitor is a protein, the protein has a targeted inhibition function on the complement activation, and the amino acid sequence of the protein comprises CRIg extracellular domain and complement inhibiting domain; the amino acid sequence of the protein is consist by the CRIg extracellular domain and the complement inhibiting domain connected directly, or indirectly through a linker which can connect the two domains;

The complement inhibiting domain could be any one or several kinds from the combination of factor H, C1 inhibiting protein, C4 binding protein, factor I, S protein, clusterin, complement membrane regulatory protein CD35/CR1, CD46/MCP, CD55/DAF, CD59 or full-length or functional fragment of CRIg itself;

The linker is preferably flexible linked peptide segment, but other linkers may also work.

The inhibitor targeting specific complement provided by the present invention use two unique characteristics of CRIg, (through specific recognition of C3b and inhibition of the activation of C3 convertase, CRIg can generated inhibiting effect in the early stage of the complement cascade, and the function site of CRIg is located in the extracellular region), the CRIg extracellular domain genes are cloned and give a fusion expression with other complement regulatory proteins. Through specific targeting effect of CRIg and C3b/iC3b, the recombinant connected complement regulatory proteins can be transferred to the local complement activation site to inhibit the activation of complement thus to prevent and treat diseases.

The gene sequence of the CRIg extracellular domain is shown as SEQ ID NO 9, and its amino acid sequence is shown as SEQ ID NO 10.

Furthermore, the other part connected with CRIg includes all components which can inhibit the complement activation, such as complement regulatory protein C1-INH, C4BP, factor I, factor H, S-protein Clusterin, CD35/CR1, CD46/MCP, CD55/DAF and CD59, even the full-length or partial sequence of CRIg itself. The connecting ways include directly connecting or indirectly connecting by other molecules through physical, chemical or biological means etc.

That is, CRIg is connected with different kinds of complement inhibitors including which in the blood circulation such as the C1-INH (C1 inhibitor), C4BP (C4 binding protein), factor I, factor H, S-protein and Clusterin (aggregation protein), and complement membrane regulatory protein expressed on the surface of the cell membrane including CD35/CR1, CD46/MCP, CD55 DAF and CD59, even CRIg itself and other material with complement inhibiting function.

The connection mode of CRIg with other complement inhibitors comprises:

(1) connecting directly, without any other linker;
(2) connecting through the biological method;
(3) connecting through the chemical method.

Preferably, the protein is comprised of CRIg and factor H (fH).

The present invention takes examples of directly connecting of CRIg extracellular domain with the factor H (fH) domain which obtains the recombinant protein CRIg-fH, or indirectly connecting by flexible linked peptide segment (Ser1Gly4)3 which obtains the recombinant protein CRIg-L-fH, to describe the inhibitory effect of the recombinant proteins CRIg-fH and CRIg-L-fH.

In one embodiment of the present invention, the protein is comprised of CRIg extracellular domain, factor H and the linker between the two.

In another embodiment of the present invention, the amino acid sequence of the protein is shown as SEQ ID NO2 or SEQ ID NO4.

The present invention provides the nucleic acids encoding the above protein. Preferably, the nucleotide encoding sequence is shown as SEQ ID NO 1 or SEQ ID NO 3.

The nucleic acid encoding proteins having the function of inhibiting complement activation as the inhibitor targeting specific complement, and containing the encoded CRIg and complement inhibitor sequence.

The present invention also provides a vector containing the nucleic acid mentioned above. Taking CRIg-fH and CRIg-(Gly$_4$Ser)$_3$-fH as examples, the vector contains base sequence of the nucleic acid shown as SEQ ID NO 1 or SEQ ID NO 3.

The present invention also provides a cell containing the nucleic acid mentioned above.

The present invention also provides a preparation method of the inhibitor targeting specific complement, wherein, the method comprises connecting the protein polypeptides of the CRIg extracellular domain and the complement inhibiting domain directly or indirectly by gene engineering technology.

The amino acid sequence of the CRIg extracellular domain protein is shown as SEQ ID NO 10;

The complement inhibiting domain could be any one or several kinds from the combination of factor H, C1 inhibiting protein, C4 binding protein, factor I, S protein, clusterin, complement membrane regulatory protein CD35/CR1, CD46/MCP, CD55/DAF, CD59 or full-length or functional fragment of CRIg itself;

The gene engineering technology comprises:

Connecting the nucleic acid sequence encoding the CRIg extracellular domain and the nucleic acid sequence encoding the complement inhibiting domain directly or indirectly through the nucleic acid sequence encoding the flexible linked peptide segment by gene splicing overlap extension PCR (SOE PCR), then inserting the fusion sequence into eukaryotic expression vector, inducing the protein expression of the inhibitor targeting specific complement through eucaryotic protein expression system, and then finally purifying the resulting protein.

Protein expression system is consist by the host system, exogenous gene, vector and the like, which can realize the expression of the exogenous gene in the host. The host is the organism to express the protein, which can be bacterial, yeast, plant cell, animal cell, etc. Different sources are suitable for different proteins expression due to different characteristics of various organisms. The species of the vectors is conformed to the host. According to the different host, the vectors can be divided into prokaryotic (bacterial) expression vectors, yeast expression vectors, plant expression vectors, mammalian expression vectors, insect expression vectors and so on. Vectors contain exogenous gene fragment, which can be expressed in the host through the meditation of vector.

The protein of the present invention can use the gene engineering technology, preferably connecting CRIg protein and factor H protein. The amino acid sequence of CRIg protein is shown as SEQ ID NO 6; the amino acid sequence of factor H protein is shown as SEQ ID NO 8. The amino acid residues can also be connected one by one in accordance with the protein sequence.

The nucleic acid of the present invention can use the gene engineering technology, preferably connecting the encoding sequences of CRIg protein and factor H protein, or connecting the bases one by one in accordance with nucleic acid sequence.

The present invention provides an inhibitor targeting specific complement, and the application of the above protein in preparing drugs to inhibit the complement activation, or protect cells from the attack of complement and increase hematocrit.

The present invention provides the application of the inhibitor targeting specific complement in the preparation of drugs for protecting the blood cells in patients with paroxysmal nocturnal hemoglobinuria. It also can be used in the preparation of drugs or chemicals for protecting the cells attacked by complement from complement attack of other diseases, such as membranoproliferative glomerulonephritis, atypical soluble hemorrhagic uremic syndrome and age-related macular degeneration.

The present invention also provides a drug, wherein the active ingredient of the drug is the protein used as inhibitor targeting specific complement, preferably, the drug contains domains of CRIg and factor H. The drug is an inhibitor of the complement activation. The drug contains the proteins with amino acid sequence shown as SEQ ID NO 2 or SEQ ID NO 4.

The drug chose the protein purified and obtained from the secretor expression in eukaryotic systems, in vivo and in vitro experiment confirmed that it has the targeted complement inhibiting function and good drug binding properties. The drug was demonstrated in vitro experiments using PNH patients erythrocytes, in which the drug showed a IC50 less than 100 nM. It was showed in vivo experiments the mesangioproliferative glomerulonephritis of rat was significantly attenuated by the drug treatment.

The pharmaceutical dosage form of the drug is preferably for injection. Other dosage forms can also be used, such as external coating, and the like.

The mode of administration of the drug, include:

(1) direct administration.

(2) through vector system that can carry or express the drug administration.

CRIg-fH, the targeted specific complement system inhibitor provided by the present invention was compare with another targeting complement inhibitor, CR2-CD59. The affinity constant (Ka) of CR2-CD59 is 3 times more than CRIg-fH ($1.093\times10^4$ to CRIg-fH, $3.45\times10^4$ 1/Ms to CR2-CD59), the dissociation constant (Kd) of CR2-CD59 is 46 times more than CRIg-fH ($3.656\times10^{-3}$ to CRIg-L-fH, 0.169 1/s to CR2-CD59), thus the equilibrium dissociation constant ($K_D$) of CRIg-fH is less than 1/15 to CR2-CD5, that means CRIg-fH has better pharmacologically activity. For although the binding speed of CRIg-L-fH to C3b/iC3b is only ⅓ of CR2-CD59, but once bound, it's hard to dissociate, so the frequency of administration can be reduced, which will greatly benefit the long-term patients of PNH. For lack of CR2-fH data, and the targeting function parts are CRIg and CR2 but not CD59 and fH, it has a certain degree of the comparability in the both.

There is a lack of the data from another targeting complement inhibitor CRIg-Fc currently. But considering that CRIg can't inhibit the degradation of C3 convertase, and hasn't the activity of promotion to factor I (like the factor H) of C3b degradation, it is supposed that CRIg only has very weak complement inhibiting activity. By comparison, the CRIg was connected with fH instead of antibody section Fc, so it will have better complement inhibiting effect.

Compared with the non-targeting complement inhibitor miniFH, the advantage of CRIg-fH is more obvious, it has not only the targeting but also the better affinity constant, and its $K_D$ is ⅓ to miniFH $K_D$.

More importantly, our experiment proved CRIg-L-fH can inhibit both AP and CP of complement, but all the other complement inhibitors mentioned above can only inhibit CP of complement.

Example 1: The Construction, Eukaryotic Expression and Purification of CRIg-fH and CRIg-L-fH Protein Expression Vectors 1. Instruments and Materials Mastercycler pro-Eppendorf PCR instrument (from Eppendorf), DK-8D Electro-Thermostatic Water Cabinet (from Shanghai Jinghong Experimental Equipment Co., Ltd.), IQ350 gel imaging system (from GE Healthcare), $CO_2$ cell culture incubator (from Thermo Scientific Company), FR-980A biological electrophoretic image analysis system (from Furi Technology Company), BioRAD Mini protein Tera system (from BioRAD), NanoVue R A/DNA concentration/purity detector (from IKA)

2. Experimental Method 2.1. Gene Cloning and Vector Construction

Since CRIg is the complement receptor high-abundance expressed on the surface of macrophages, the total RNA from human histiocytic lymphoma cell line U937 is extracted and reverse transcript to cDNA by Trizol method. According to reported literatures, the protein sequence of CRIg extracellular domain is found from NCBI protein database (NP_001171759.1, residues 19-137), the nucleic acid sequence of CRIg gene is found from NCBI gene database (NM_001184830.1). Design the upstream and downstream primer sequence to clone the CRIg extracellular domain, obtain the nucleic acid sequence of the CRIg extracellular domain from the cDNA of U937 by PCR amplification, connect it to the pMD18 T vector, transfer, screen with blue white blot test for positive clones, pick the positive colonies, expand cultivation and then send to sequencing.

Similarly, since the complement regulating protein factor H has higher expression in liver cells, the total RNA from human hepatoma cell line HepG2 is extracted and reverse transcript to cDNA by Trizol method. According to reported literatures about the factor H SCR1-5 domain (NP_001171759.1, residues 19-137), the protein sequence is found from NCBI protein database, the corresponding nucleic acid sequence of factor H gene is found from NCBI gene database. Design the upstream and downstream primer sequence to clone the FH SCR1-5 domain, obtain the nucleic acid sequence of the FH SCR1-5 domain from the cDNA of HepG2 by PCR amplification, connect it to the pMD18 T vector, transfer, screen with blue white blot test for positive clones, pick the positive colonies, expand cultivation and then send to sequencing. Select the correct clone from the sequencing result, extract the plasmid as the template for gene splicing overlap extension PCR.

Furthermore, connect the CRIg extracellular domain and the SCR1-5 domain of factor H directly (CRIg-fH) or indirectly (CRIg-L-fH) through flexible linked peptide sequence (SerGly4) 3 by gene splicing overlap extension PCR (SOE PCR).

The principle of gene splicing overlap extension PCR is as following, primes having complementary ends are used to form the PCR products with double chains which contains overlapping region, then in the second round of PCR amplification reaction, through extension of the overlap chains, the extension fragments from different sources is overlapped and split to construct the fusion sequence including CRIg extracellular domain, SCR1-5 domain of factor H and the linker sequence (flexible linked peptide sequence) (L, (Ser1Gly4)3) (TCTGGTGGCGGTGGCTCCGGCGGAGGTGGGTCCGGTGGCGGCGGA). The fusion sequences are inserted into the eukaryotic expression vectors in pHLsec, bi-directional sequence the insertion sequence, and the vectors are named as pHLsec-CRIg-fH and pHLsec-CRIg-L-fH.

```
CRIg nucleic acid sequence (SEQ ID NO 5):
ATGGGGATCTTACTGGGCCTGCTACTCCTGGGGCACCTAACAGTGGACA

CTTATGGCCGTCCCATCCTGGAAGTGCCAGAGAGTGTAACAGGACCTT

GGAAAGGGGATGTGAATCTTCCCTGCACCTATGACCCCCTGCAAGGCT

ACACCCAAGTCTTGGTGAAGTGGCTGGTACAACGTGGCTCAGACCCTG

TCACCATCTTTCTACGTGACTCTTCTGGAGACCATATCCAGCAGGCAAA

GTACCAGGGCCGCCTGCATGTGAGCCACAAGGTTCCAGGAGATGTATC

CCTCCAATTGAGCACCCTGGAGATGGATGACCGGAGCCACTACACGTG

TGAAGTCACCTGGCAGACTCCTGATGGCAACCAAGTCGTGAGAGATAA

GATTACTGAGCTCCGTGTCCAGAAACTCTCTGTCTCCAAGCCCACAGTG

ACAACTGGCAGCGGTTATGGCTTCACGGTGCCCCAGGGAATGAGGATT

AGCCTTCAATGCCAGGCTCGGGGTTCTCCTCCCATCAGTTATATTTGGTA
```

-continued

```
TAAGCAACAGACTAATAACCAGGAACCCATCAAAGTAGCAACCCTAAG

TACCTTACTCTTCAAGCCTGCGGTGATAGCCGACTCAGGCTCCTATTTCT

GCACTGCCAAGGGCCAGGTTGGCTCTGAGCAGCACAGCGACATTGTGA

AGTTTGTGGTCAAAGACTCCTCAAAGCTACTCAAGACCAAGACTGAGG

CACCTACAACCATGACATACCCCTTGAAAGCAACATCTACAGTGAAGC

AGTCCTGGGACTGGACCACTGACATGGATGGCTACCTTGGAGAGACCA

GTGCTGGGCCAGGAAAGAGCCTGCCTGTCTTTGCCATCATCCTCATCAT

CTCCTTGTGCTGTATGGTGGTTTTTACCATGGCCTATATCATGCTCTGTC

GGAAGACATCCCAACAAGAGCATGTCTACGAAGCAGCCAGGGCACATGC

CAGAGAGGCCAACGACTCTGGAGAAACCATGAGGGTGGCCATCTTCGC

AAGTGGCTGCTCCAGTGATGAGCCAACTTCCCAGAATCTGGGCAACAA

CTACTCTGATGAGCCCTGCATAGGACAGGAGTACCAGATCATCGCCCAG

ATCAATGGCAACTACGCCCGCCTGCTGGACACAGTTCCTCTGGATTATG

AGTTTCTGGCCACTGAGGGCAAAAGTGTCTGTTAA

CRIg protein sequence (SEQ ID NO 6):
MGILLGLLLLGHLTVDTYGRPILEVPESVTGPWKGDVNLPCTYDPLQGYT

QVLVKWLVQRGSDPVTIFLRDSSGDHIQQAKYQGRLHVSHKVPGDVSLQ

LSTLEMDDRSHYTCEVTWQTPDGNQVVRDKITELRVQKLSVSKPTVTTGS

GYGFTVPQGMRISLQCQARGSPPISYIWYKQQTNNQEPIKVATLSTLLFK

PAVIADSGSYFCTAKGQVGSEQHSDIVKFVVKDSSKLLKTKTEAPTTMTY

PLKATSTVKQSWDWTTDMDGYLGETSAGPGKSLPVFAIILIISLCCMVVF

TMAYIMLCRKTSQQEHVYEAARAHAREANDSGETMRVAIFASGCSSDEPT

SQNLGNNYSDEPCIGQEYQIIAQINGNYARLLDTVPLDYEFLATEGKSVC

Factor H nucleic acid sequence (SEQ ID NO 7):
ATGAGACTTCTAGCAAAGATTATTTGCCTTATGTTATGGGCTATTTGTGT

AGCAGAAGATTGCAATGAACTTCCTCCAAGAAGAAATACAGAAATTCT

GACAGGTTCCTGGTCTGACCAAACATATCCAGAAGGCACCCAGGCTAT

CTATAAATGCCGCCCTGGATATAGATCTCTTGGAAATGTAATAATGGTAT

GCAGGAAGGGAGAATGGGTTGCTCTTAATCCATTAAGGAAATGTCAGA

AAAGGCCCTGTGGACATCCTGGAGATACTCCTTTTGGTACTTTTACCCTT

ACAGGAGGAAATGTGTTTGAATATGGTGTAAAAGCTGTGTATACATGTA

ATGAGGGGTATCAATTGCTAGGTGAGATTAATTACCGTGAATGTGACAC

AGATGGATGGACCAATGATATTCCTATATGTGAAGTTGTGAAGTGTTTAC

CAGTGACAGCACCAGAGAATGGAAAAATTGTCAGTAGTGCAATGGAAC

CAGATCGGGAATACCATTTTGGACAAGCAGTACGGTTTGTATGTAACTC

AGGCTACAAGATTGAAGGAGATGAAGAAATGCATTGTTCAGACGATGG

TTTTTGGAGTAAAGAGAAACCAAAGTGTGTGGAAATTTCATGCAAATC

CCCAGATGTTATAAATGGATCTCCTATATCTCAGAAGATTATTTATAAGG

AGAATGAACGATTTCAATATAAATGTAACATGGGTTATGAATACAGTGAA

AGAGGAGATGCTGTATGCACTGAATCTGGATGGCGTCCGTTGCCTTCAT

GTGAAGAAAAATCATGTGATAATCCTTATATTCCAAATGGTGACTACTCA
```

-continued
```
CCTTTAAGGATTAAACACAGAACTGGAGATGAAATCACGTACCAGTGT
AGAAATGGTTTTTATCCTGCAACCCGGGGAAATACAGCAAAATGCACA
AGTACTGGCTGGATACCTGCTCCGAGATGTACCTTGAAACCTTGTGATT
ATCCAGACATTAAACATGGAGGTCTATATCATGAGAATATGCGTAGACCA
TACTTTCCAGTAGCTGTAGGAAAATATTACTCCTATTACTGTGATGAACA
TTTTGAGACTCCGTCAGGAAGTTACTGGGATCACATTCATTGCACACAA
GATGGATGGTCGCCAGCAGTACCATGCCTCAGAAAATGTTATTTTCCTTA
TTTGGAAAATGGATATAATCAAAATCATGGAAGAAAGTTTGTACAGGGT
AAATCTATAGACGTTGCCTGCCATCCTGGCTACGCTCTTCCAAAAGCGC
AGACCACAGTTACATGTATGGAGAATGGCTGGTCTCCTACTCCCAGATG
CATCCGTGTCAAAACATGTTCCAAATCAAGTATAGATATTGAGAATGGG
TTTATTTCTGAATCTCAGTATACATATGCCTTAAAAGAAAAAGCGAAATA
TCAATGCAAACTAGGATATGTAACAGCAGATGGTGAAACATCAGGATCA
ATTACATGTGGGAAAGATGGATGGTCAGCTCAACCCACGTGCATTAAAT
CTTGTGATATCCCAGTATTTATGAATGCCAGAACTAAAAATGACTTCACA
TGGTTTAAGCTGAATGACACATTGGACTATGAATGCCATGATGGTTATGA
AAGCAATACTGGAAGCACCACTGGTTCCATAGTGTGTGGTTACAATGGT
TGGTCTGATTTACCCATATGTTATGAAAGAGAATGCGAACTTCCTAAAAT
AGATGTACACTTAGTTCCTGATCGCAAGAAAGACCAGTATAAAGTTGGA
GAGGTGTTGAAATTCTCCTGCAAACCAGGATTTACAATAGTTGGACCTA
ATTCCGTTCAGTGCTACCACTTTGGATTGTCTCCTGACCTCCCAATATGT
AAAGAGCAAGTACAATCATGTGGTCCACCTCCTGAACTCCTCAATGGG
AATGTTAAGGAAAAAACGAAAGAAGAATATGGACACAGTGAAGTGG
GGAATATTATTGCAATCCTAGATTTCTAATGAAGGGACCTAATAAAATTC
AATGTGTTGATGGAGAGTGGACAACTTTACCAGTGTGTATTGTGGAGGA
GAGTACCTGTGGAGATATACCTGAACTTGAACATGGCTGGGCCCAGCTT
TCTTCCCCTCCTTATTACTATGGAGATTCAGTGGAATTCAATTGCTCAGA
ATCATTTACAATGATTGGACACAGATCAATTACGTGTATTCATGGAGTAT
GGACCCAACTTCCCCAGTGTGTGGCAATAGATAAACTTAAGAAGTGCA
AATCATCAAATTTAATTATACTTGAGGAACATTTAAAAAACAAGAAGGA
ATTCGATCATAATTCTAACATAAGGTACAGATGTAGAGGAAAAGAAGGA
TGGATACACAGTCTGCATAAATGGAAGATGGGATCCAGAAGTGAAC
TGCTCAATGGCACAAATACAATTATGCCCACCTCCACCTCAGATTCCCA
ATTCTCACAATATGACAACCACACTGAATTATCGGGATGGAGAAAAAGT
ATCTGTTCTTTGCCAAGAAAATTATCTAATTCAGGAAGGAGAAGAAATT
ACATGCAAAGATGGAAGATGGCAGTCAATACCACTCTGTGTTGAAAAA
ATTCCATGTTCACAACCACCTCAGATAGAACACGGAACCATTAATTCAT
CCAGGTCTTCACAAGAAAGTTATGCACATGGGACTAAATTGAGTTATAC
TTGTGAGGGTGGTTTCAGGATATCTGAAGAAAATGAAACAACATGCTA
CATGGGAAAATGGAGTTCTCCACCTCAGTGTGAAGGCCTTCCTTGTAAA
TCTCCACCTGAGATTTCTCATGGTGTTGTAGCTCACATGTCAGACAGTTA
```

-continued
```
TCAGTATGGAGAAGAAGTTACGTACAAATGTTTTGAAGGTTTTGGAATT
GATGGGCCTGCAATTGCAAAATGCTTAGGAGAAAAATGGTCTCACCCT
CCATCATGCATAAAAACAGATTGTCTCAGTTTACCTAGCTTTGAAAATG
CCATACCCATGGGAGAGAAGAAGGATGTGTATAAGGCGGGTGAGCAAG
TGACTTACACTTGTGCAACATATTACAAAATGGATGGAGCCAGTAATGT
AACATGCATTAATAGCAGATGGACAGGAAGGCCAACATGCAGAGACAC
CTCCTGTGTGAATCCGCCCACAGTACAAAATGCTTATATAGTGTCGAGA
CAGATGAGTAAATATCCATCTGGTGAGAGAGTACGTTATCAATGTAGGA
GCCCTTATGAAATGTTTGGGGATGAAGAAGTGATGTGTTTAAATGGAAA
CTGGACGGAACCACCTCAATGCAAAGATTCTACAGGAAAATGTGGGCC
CCCTCCACCTATTGACAATGGGGACATTACTTCATTCCCGTTGTCAGTAT
ATGCTCCAGCTTCATCAGTTGAGTACCAATGCCAGAACTTGTATCAACT
TGAGGGTAACAAGCGAATAACATGTAGAAATGGACAATGGTCAGAACC
ACCAAAATGCTTACATCCGTGTGTAATATCCCGAGAAATTATGGAAAATT
ATAACATAGCATTAAGGTGGACAGCCAAACAGAAGCTTTATTCGAGAA
CAGGTGAATCAGTTGAATTTGTGTGTAAACGGGGATATCGTCTTTCATC
ACGTTCTCACACATTGCGAACAACATGTTGGGATGGGAAACTGGAGTA
TCCAACTTGTGCAAAAAGATAG
```

Factor H protein sequence (SEQ ID NO 8):
MRLLAKIICLMLWAICVAEDCNELPPRRNTEILTGSWSDQTYPEGTQAIY
KCRPGYRSLGNVIMVCRKGEWVALNPLRKCQKRPCGHPGDTPFGTFTLTG
GNVFEYGVKAVYTCNEGYQLLGEINYRECDTDGWTNDIPICEVVKCLPVT
APENGKIVSSAMEPDREYHFGQAVRFVCNSGYKIEGDEEMHCSDDGFWS
KEKPKCVEISCKSPDVINGSPISQKIIYKENERFQYKCNMGYEYSERGDA
VCTESGWRPLPSCEEKSCDNPYIPNGDYSPLRIKHRTGDEITYQCRNGFY
PATRGNTAKCTSTGWIPAPRCTLKPCDYPDIKHGGLYHENMRRPYFPVAV
GKYYSYYCDEHFETPSGSYWDHIHCTQDGWSPAVPCLRKCYFPYLENGYN
QNHGRKFVQGKSIDVACHPGYALPKAQTTVTCMENGWSPTPRCIRVKTCS
KSSIDIENGFISESQYTYALKEKAKYQCKLGYVTADGETSGSITCGKDGW
SAQPTCIKSCDIPVFMNARTKNDFTWFKLNDTLDYECHDGYESNTGSTTG
SIVCGYNGWSDLPICYERECELPKIDVHLVPDRKKDQYKVGEVLKFSCKP
GFTIVGPNSVQCYHFGLSPDLPICKEQVQSCGPPPELLNGNVKEKTKEEY
GHSEVVEYYCNPRFLMKGPNKIQCVDGEWTTLPVCIVEESTCGDIPELEH
GWAQLSSPPYYYGDSVEFNCSESFTMIGHRSITCIHGVWTQLPQCVAIDK
LKKCKSSNLIILEEHLKNKKEFDHNSNIRYRCRGKEGWIHTVCINGRWDP
EVNCSMAQIQLCPPPPQIPNSHNMTTTLNYRDGEKVSVLCQENYLIQEGE
EITCKDGRWQSIPLCVEKIPCSQPPQIEHGTINSSRSSQESYAHGTKLSY
TCEGGFRISEENETTCYMGKWSSPPQCEGLPCKSPPEISHGVVAHMSDSY
QYGEEVTYKCFEGFGIDGPAIAKCLGEKWSHPPSCIKTDCLSLPSFENAI
PMGEKKDVYKAGEQVTYTCATYYKMDGASNVTCINSRWTGRPTCRDTSCV
NPPTVQNAYIVSRQMSKYPSGERVRYQCRSPYEMFGDEEVMCLNGNWTEP
```

-continued

PQCKDSTGKCGPPPPIDNGDITSFPLSVYAPASSVEYQCQNLYQLEGNKR

ITCRNGQWSEPPKCLHPCVISREIMENYNIALRWTAKQKLYSRTGESVEF

VCKRGYRLSSRSHTLRTTCWDGKLEYPTCAKR

CRIg extracellular domain
Nucleic acid sequence (357 bps) (SEQ ID NO 9):
ggccgtcccatcctggaagtgccagagagtgtaacaggaccttggaaagg ggatgtgaatcttccctgcacctatgacccctgcaaggctacacccaag tcttggtgaagtggctggtacaacgtggctcagaccctgtcaccatcttt ctacgtgactcttctggagaccatatccagcaggcaaagtaccagggccg cctgcatgtgagccacaaggttccaggagatgtatccctccaattgagca ccctggagatggatgaccggagccactacacgtgtgaagtcacctggcag actcctgatggcaaccaagtcgtgagagataagattactgagctccgtgt ccagaaa Protein sequence (119 aa) (SEQ ID NO 10)
GRPILEVPESVTGPWKGDVNLPCTYDPLQGYTQVLVKWLVQRGSDPVTIF

LRDSSGDHIQQAKYQGRLHVSHKVPGDVSLQLSTLEMDDRSHYTCEVTWQ

TPDGNQVVRDKITELRVQK

FactorH SCR1-5 domain
Nucleic acid sequence (915 bp) (SEQ ID NO 11):
Gaagattgcaatgaacttcctccaagaagaaatacagaaattctgacagg ttcctggtctgaccaaacatatccagaaggcacccaggctatctataaat gccgccctggatatagatctcttggaaatgtaataatggtatgcaggaag ggagaatgggttgctcttaatccattaaggaaatgtcagaaaaggccctg tggacatcctggagatactccttttggtacttttacccttacaggaggaa atgtgtttgaatatggtgtaaaagctgtgtatacatgtaatgagggtat caattgctaggtgagattaattaccgtgaatgtgacacagatggatggac caatgatattcctatatgtgaagttgtgaagtgtttaccagtgacagcac cagagaatggaaaaattgtcagtagtgcaatggaaccagatcgggaatac cattttggacaagcagtacggtttgtatgtaactcaggctacaagattga aggagatgaagaaatgcattgttcagacgatggttttggagtaaagaga aaccaaagtgtgtggaaatttcatgcaaatccccagatgttataaatgga tctcctatatctcagaagattatttataaggagaatgaacgatttcaata taaatgtaacatgggttatgaatacagtgaaagaggagatgctgtatgca ctgaatctggatggcgtccgttgccttcatgtgaagaaaatcatgtgat aatccttatattccaaatggtgactactcaccttttaaggattaaacacag aactggagatgaaatcacgtaccagtgtagaaatggttttttatcctgcaa cccggggaaatacagcaaaatgcacaagtactggctggatacctgctccg agatgtaccttgaaa Protein sequence (305 aa) (SEQ ID NO 12):
EDCNELPPRRNTEILTGSWSDQTYPEGTQAIYKCRPGYRSLGNVIMVCRK

GEWVALNPLRKCQKRPCGHPGDTPFGTFTLTGGNVFEYGVKAVYTCNEG

YQLLGEINYRECDTDGWTNDIPICEVVKCLPVTAPENGKIVSSAMEPDRE

YHFGQAVRFVCNSGYKIEGDEEMHCSDDGFWSKEKPKCVEISCKSPDVIN

GSPISQKIIYKENERFQYKCNMGYEYSERGDAVCTESGWRPLPSCEEKSC

DNPYIPNGDYSPLRIKHRTGDEITYQCRNGFYPATRGNTAKCTSTGWIPA

PRCTLK 2.2 The Establishment of Eukaryotic Protein Expression System

The logarithmic growth phase 293FT cells are spread in cell culture dishes with diameter of 15 cm by the cell density of $1.2 \times 10^7$ to each dish, then respectively transfect pHLsec-CRIg-L-fH and pHLsec-CRIg-fH plasmids by PEI method. After cultured at 37° C., 5% $CO_2$ in culture incubator for 6 hours, replace with the 293 expression culture medium (from Invitrogen Company). Keep on culturing for three days, then collect the cell supernatants and remove the cells and cell debris by centrifugation.

2.3 Protein Affinity Purification, Dialysis and Sucrose Concentration

Through $Ni^{2+}$ column affinity purification method, the CRIg-fH and CRIg-L-fH in the supernatant of the cells are purified and eluted to buffer, transfer to the dialysis tube (from Novagen Company), and then the buffer is replaced with PBS (phosphate buffer), after concentration by sucrose absorption method, dialysis by PBS.

3. Experimental Results

Through the method mentioned above, CRIg-L-fH and CRIg-fH fusion proteins are obtained from induced expression and purification by using the eukaryotic expression system. PAGE electrophoresis (polyacrylamide gelelectrophoresis) shows only a single strip, the concentration can reach 1-2 mg/ml after concentration as shown in FIG. 1.

The related sequences are shown as following:

CRIg-fH nucleic acid sequence (SEQ ID NO 1):
ATGGGCCGTCCCATCCTGGAAGTGCCAGAGAGTGTAACAGGACCTTGG

AAAGGGGATGTGAATCTTCCCTGCACCTATGACCCCCTGCAAGGCTACA

CCCAAGTCTTGGTGAAGTGGCTGGTACAACGTGGCTCAGACCCTGTCA

CCATCTTTCTACGTGACTCTTCTGGAGACCATATCCAGCAGGCAAAGTA

CCAGGGCCGCCTGCATGTGAGCCACAAGGTTCCAGGAGATGTATCCCT

CCAATTGAGCACCCTGGAGATGGATGACCGGAGCCACTACACGTGTGA

AGTCACCTGGCAGACTCCTGATGGCAACCAAGTCGTGAGAGATAAGAT

TACTGAGCTCCGTGTCCAGAAAGAAGATTGCAATGAACTTCCTCCAAG

AAGAAATACAGAAATTCTGACAGGTTCCTGGTCTGACCAAACATATCCA

GAAGGCACCCAGGCTATCTATAAATGCCGCCCTGGATATAGATCTCTTGG

AAATGTAATAATGGTATGCAGGAAGGGAGAATGGGTTGCTCTTAATCCA

TTAAGGAAATGTCAGAAAAGGCCCTGTGGACATCCTGGAGATACTCCT

TTTGGTACTTTTACCCTTACAGGAGGAAATGTGTTTGAATATGGTGTAAA

AGCTGTGTATACATGTAATGAGGGGTATCAATTGCTAGGTGAGATTAATT

ACCGTGAATGTGACACAGATGGATGGACCAATGATATTCCTATATGTGA

AGTTGTGAAGTGTTTACCAGTGACAGCACCAGAGAATGGAAAAATTGT

CAGTAGTGCAATGGAACCAGATCGGGAATACCATTTTGGACAAGCAGT

ACGGTTTGTATGTAACTCAGGCTACAAGATTGAAGGAGATGAAGAAAT

GCATTGTTCAGACGATGGTTTTTGGAGTAAAGAGAAACCAAAGTGTGT

GGAAATTTCATGCAAATCCCCAGATGTTATAAATGGATCTCCTATATCTC

AGAAGATTATTTATAAGGAGAATGAACGATTTCAATATAAATGTAACATG

GGTTATGAATACAGTGAAAGAGGAGATGCTGTATGCACTGAATCTGGAT

GGCGTCCGTTGCCTTCATGTGAAGAAAAATCATGTGATAATCCTTATATT

CCAAATGGTGACTACTCACCTTTAAGGATTAAACACAGAACTGGAGAT

GAAATCACGTACCAGTGTAGAAATGGTTTTTATCCTGCAACCCGGGGAA

ATACAGCAAAATGCACAAGTACTGGCTGGATACCTGCTCCGAGATGTAC

CTTGAAATAA

CRIg-fH protein sequence (SEQ ID NO 2):
MGRPILEVPESVTGPWKGDVNLPCTYDPLQGYTQVLVKWLVQRGSDPVT

IFLRDSSGDHIQQAKYQGRLHVSHKVPGDVSLQLSTLEMDDRSHYTCEVT

WQTPDGNQVVRDKITELRVQKEDCNELPPRRNTEILTGSWSDQTYPEGTQ

AIYKCRPGYRSLGNVIMVCRKGEWVALNPLRKCQKRPCGHPGDTPFGTFT

LTGGNVFEYGVKAVYTCNEGYQLLGEINYRECDTDGWTNDIPICEVVKCL

PVTAPENGKIVSSAMEPDREYHFGQAVRFVCNSGYKIEGDEEMHCSDDGF

WSKEKPKCVEISCKSPDVINGSPISQKIIYKENERFQYKCNMGYEYSERG

DAVCTESGWRPLPSCEEKSCDNPYIPNGDYSPLRIKHRTGDEITYQCRNG

FYPATRGNTAKCTSTGWIPAPRCTLKStop

CRIg-L-fH nucleic acid sequences (SEQ ID NO 3):
ATGGGCCGTCCCATCCTGGAAGTGCCAGAGAGTGTAACAGGACCTTGG

AAAGGGGATGTGAATCTTCCCTGCACCTATGACCCCCTGCAAGGCTACA

CCCAAGTCTTGGTGAAGTGGCTGGTACAACGTGGCTCAGACCCTGTCA

CCATCTTTCTACGTGACTCTTCTGGAGACCATATCCAGCAGGCAAAGTA

CCAGGGCCGCCTGCATGTGAGCCACAAGGTTCCAGGAGATGTATCCCT

CCAATTGAGCACCCTGGAGATGGATGACCGGAGCCACTACACGTGTGA

AGTCACCTGGCAGACTCCTGATGGCAACCAAGTCGTGAGAGATAAGAT

TACTGAGCTCCGTGTCCAGAAATCTGGTGGCGGTGGCTCCGGCGGAGG

TGGGTCCGGTGGCGGCGGAGAAGATTGCAATGAACTTCCTCCAAGAAG

AAATACAGAAATTCTGACAGGTTCCTGGTCTGACCAAACATATCCAGAA

GGCACCCAGGCTATCTATAAATGCCGCCCTGGATATAGATCTCTTGGAAA

TGTAATAATGGTATGCAGGAAGGGAGAATGGGTTGCTCTTAATCCATTA

AGGAAATGTCAGAAAAGGCCCTGTGGACATCCTGGAGATACTCCTTTT

GGTACTTTTACCCTTACAGGAGGAAATGTGTTTGAATATGGTGTAAAAG

CTGTGTATACATGTAATGAGGGGTATCAATTGCTAGGTGAGATTAATTAC

CGTGAATGTGACACAGATGGATGGACCAATGATATTCCTATATGTGAAG

TTGTGAAGTGTTTACCAGTGACAGCACCAGAGAATGGAAAAATTGTCA

GTAGTGCAATGGAACCAGATCGGGAATACCATTTTGGACAAGCAGTAC

GGTTTGTATGTAACTCAGGCTACAAGATTGAAGGAGATGAAGAAATGCA

TTGTTCAGACGATGGTTTTTGGAGTAAAGAGAAACCAAAGTGTGTGGA

AATTTCATGCAAATCCCCAGATGTTATAAATGGATCTCCTATATCTCAGA

AGATTATTTATAAGGAGAATGAACGATTTCAATATAAATGTAACATGGGT

TATGAATACAGTGAAAGAGGAGATGCTGTATGCACTGAATCTGGATGGC

GTCCGTTGCCTTCATGTGAAGAAAAATCATGTGATAATCCTTATATTCCA

AATGGTGACTACTCACCTTTAAGGATTAAACACAGAACTGGAGATGAA

ATCACGTACCAGTGTAGAAATGGTTTTTATCCTGCAACCCGGGGAAATA

CAGCAAAATGCACAAGTACTGGCTGGATACCTGCTCCGAGATGTACCTT

GAAATAA

CRIg-L-fH Protein sequence (SEQ ID NO 4):
MGRPILEVPESVTGPWKGDVNLPCTYDPLQGYTQVLVKWLVQRGSDPVT

IFLRDSSGDHIQQAKYQGRLHVSHKVPGDVSLQLSTLEMDDRSHYTCEVT

WQTPDGNQVVRDKITELRVQKSGGGGSGGGGSGGGGEDCNELPPRRNTE

ILTGSWSDQTYPEGTQAIYKCRPGYRSLGNVIMVCRKGEWVALNPLRKCQ

KRPCGHPGDTPFGTFTLTGGNVFEYGVKAVYTCNEGYQLLGEINYRECDT

DGWTNDIPICEVVKCLPVTAPENGKIVSSAMEPDREYHFGQAVRFVCNSG

YKIEGDEEMHCSDDGFWSKEKPKCVEISCKSPDVINGSPISQKIIYKENE

RFQYKCNMGYEYSERGDAVCTESGWRPLPSCEEKSCDNPYIPNGDYSPLR

IKHRTGDEITYQCRNGFYPATRGNTAKCTSTGWIPAPRCTLKStop

Example 2: The Kinetics Analysis and Affinity Determination of the Interaction Between CRIg-fH and CRIg-L-fH with C3 Activation Degradation Fragments 1. Instruments and Materials Biacore T200 (protein interaction analyzer, from Company GE Healthcare Company), Series S Sensor Chip NTA chip, CRIg-L-fH protein solution, C3 activation and degradation of the protein component (C3b, iC3b, C3c, C3d, from Complement Technology Company), solution HBS-N (from GE Healthcare Company)

2. Experimental Method

Surface plasmon resonance (SPR) is a technology used for analyzing the biological macromolecule interactions, which can qualitatively judge whether there is interaction between two molecules or to compare the strength of the interactions between a molecule with a variety of molecules. It can also quantitatively determine the affinity parameter (equilibrium constant) and dynamics parameter (rate constant), even thermodynamic parameters (reaction enthalpies) in real time. This technology utilizes the principle of physical optics. In the study of the interaction between two molecules, a molecule is fixed on the surface of the sensor chip, the solution of another kind of molecule is flowed through the surface of the chip. The combination of the two molecules will change the refractive index of the sensor chip surface, which can be used to detect the interaction between the two molecules. The kinetics analysis and affinity determination of the complement inhibitor CRIg-fH with C3 enzymolysis products are performed by using BIAcore T200 based on the principle of SPR. The Series S Sensor NTA chip is chosen for the CRIg-fHHi label. The experiment method is as follows:

(1) chip pre-treatment: embed the NTA sensor chip module into the BIAcore instrument, prepare HBS-N running buffer (buffer solution), open BIAcore T200 protein interaction analyzer, set up the program. Firstly, pre-inject twice of the HBS-N running buffer to clean the chip, at the temperature of 25° C., the flow rate is 120 µl/min, each injection is continued to 5 min till the baseline is flat;

(2) Ni coupling: Inject Nickel solution (0.5 mM $NiCl_2$/running buffer) once, at 25° C., the flow rate is 30 µl/min, the sustain time is 60 sec, the stability time is 30 sec;

(3) ligand coupling: the CRIg-fH fusion protein is diluted to 0.2 µg/ml ligand solution by HBS-N running buffer, inject the ligand solution once, at 25° C., the flow rate is 30 µl/min, the sustain time is 60 sec, the stability time is 30 sec.

(4) analyte injection: prepare analysis solution with gradient dilution of the C3 enzymolysis products with HBS-N running buffer, inject once of analysis solution with a specified concentration of C3 enzymolysis products, at 25° C., the flow rate is 30 µl/min, the sustain time is 2 min, the stability time is 120 sec;

(5) chip regeneration: inject once of regeneration solution (regenerating solution: 350 mM EDTA (ethylene diamine tetraacetic acid), pH8.3), at 25° C., the flow rate is 30 µl/min, the sustain time is 60 sec;

(6) repeat steps (2) to (5) for the kinetic curve determination of C3 enzymolysis products with second concentration;

(7) after the completion of the determination of all the concentration of all the C3 enzymolysis products, inject twice the regeneration solution to clean the chip till the base line is flat.

(8) the kinetic curve is simulated and the kinetic parameters (including association constant Ka, dissociation constant Kd and equilibrium dissociation constant $K_D$) are determined by BIAcore T200 v2.02 software. The Ka, Kd and $K_D$ are shown in table 1.

TABLE 1

|  | $k_a$ (1/Ms) | $k_d$ (1/s) | $K_D$ (M) |
|---|---|---|---|
| CRIg-L-fH |  |  |  |
| C3b | 1.648E4 | 3.750E-3 | 2.336E-7 |
| IC3b | 1.023E3 | 3.615E-3 | 3.513E-6 |
| C3c | 2.479E3 | 6.150E-3 | 2.492E-6 |
| C3d | — | — | — |
| CRIg-fH |  |  |  |
| C3b | 1.093E4 | 3.556E-3 | 3.346E-7 |
| IC3b | 3.327E3 | 4.055E-3 | 1.219E-6 |
| C3c | 1.051E3 | 7.155E-3 | 6.806E-6 |
| C3d | — | — | — |

3. The Experimental Results

Figure 2:
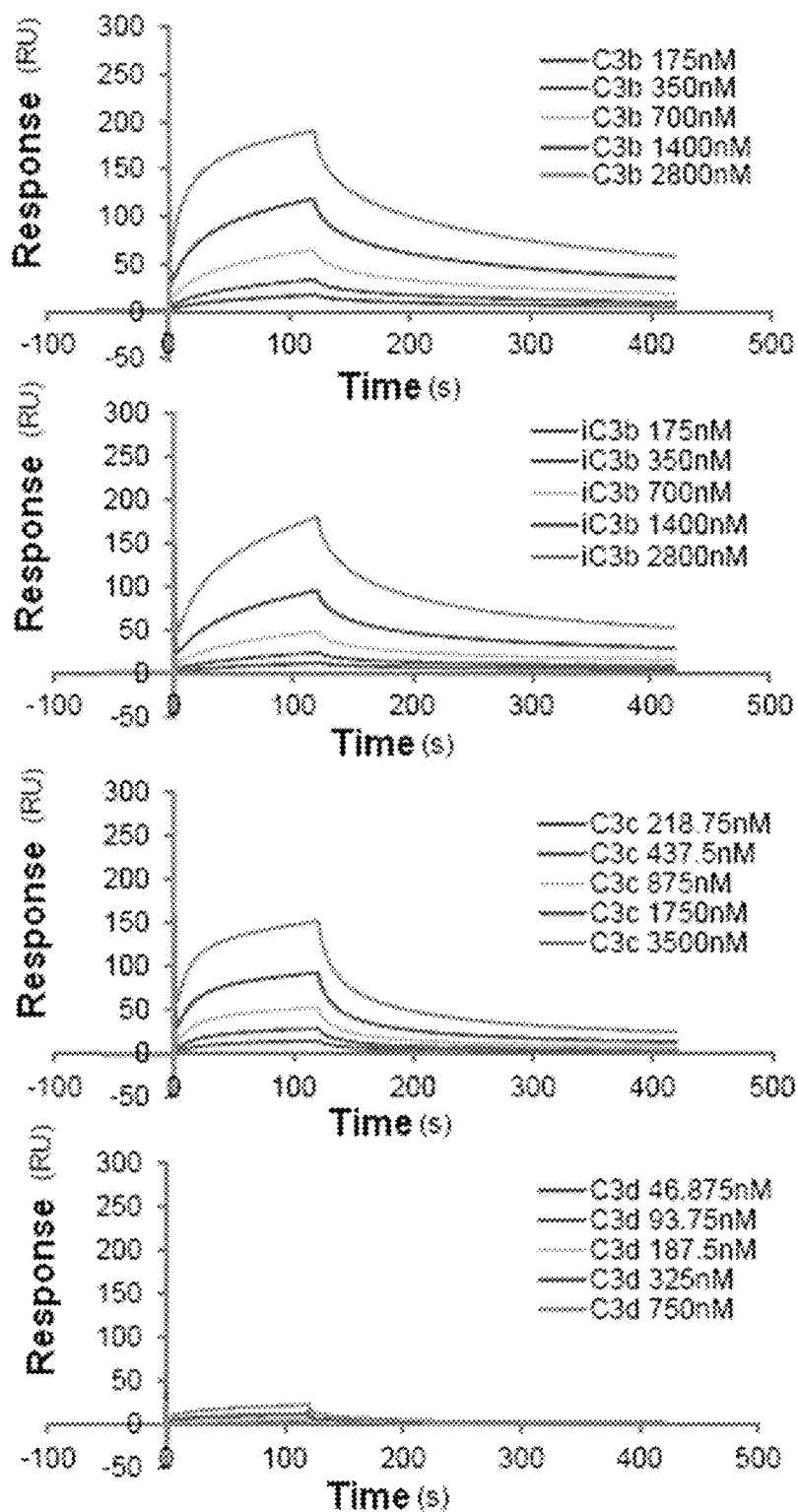
FIG. 2 is shown the kinetic analysis and determining result of binding force of the interaction between CRIg-L-fH and C3 activation degradation products C3b, iC3b, C3c, C3d.
Figure 3:
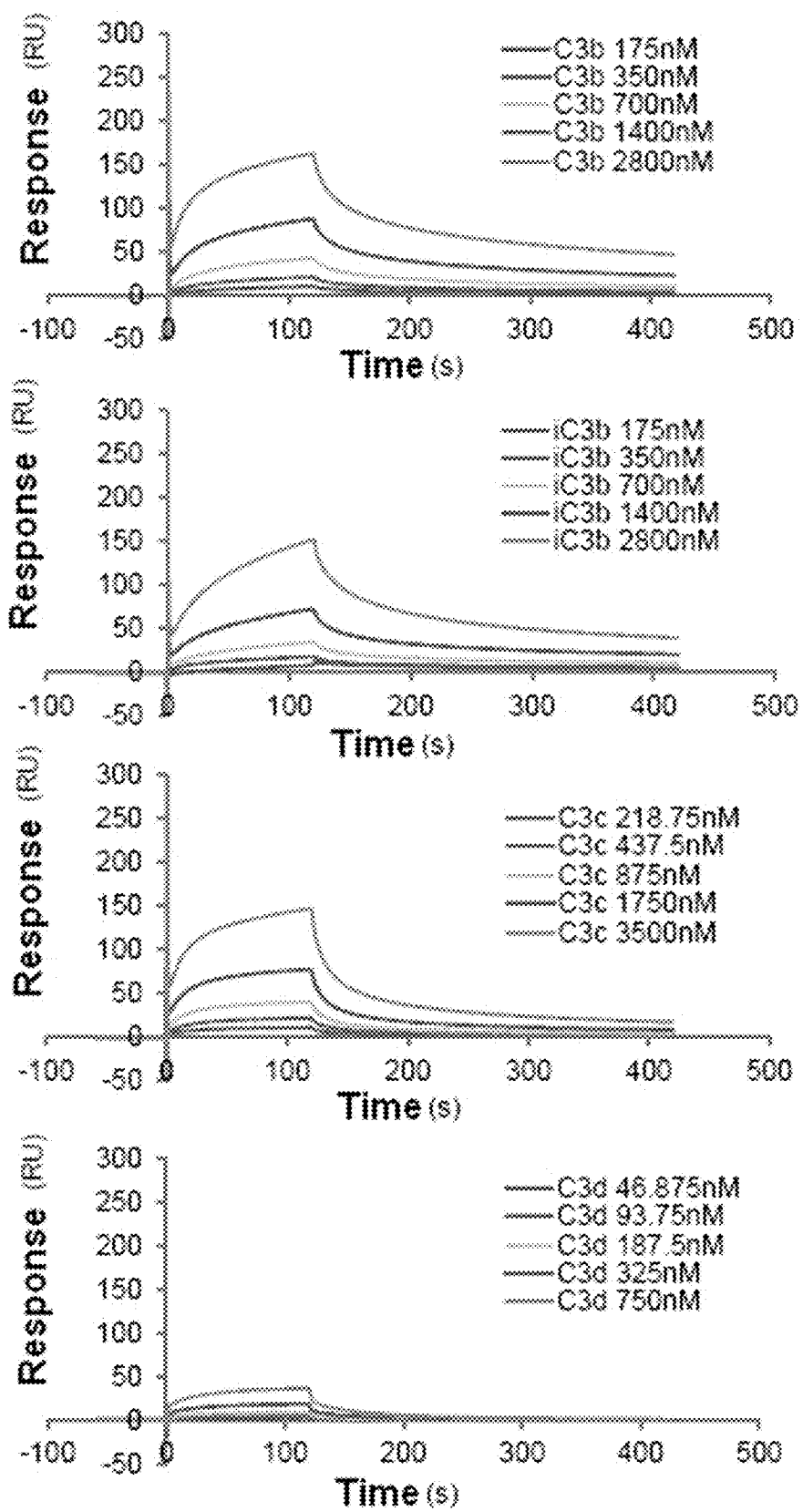
FIG. 3 is shown the kinetic analysis and determining result of binding force of the interaction between CRIg-fH and C3 activation degradation products C3b, iC3b, C3c, C3d.

See FIG. 2 (the interaction between CRIg-L-fH and C3 activation degradation products C3b, iC3b, C3c, C3d) and FIG. 3 (the schematic diagrams of the kinetic analysis and determining result of binding force about the interaction between CRIg-L-fH and C3 activation degradation products C3b, iC3b, C3c, C3d), CRIg-fH and CRIg-L-fH both have a different degree of binding with C3 activation degradation products C3b, iC3b, C3c, C3d. The binding force of CRIg-L-fH is stronger, and it is chosen to in further function experiments animal models.

Example 3: CRIg-L-fH Protects PNH Erythrocytes from Complement AP and CP Induced Hemolysis 1. Instruments and Materials Erythrocytes of seven PNH patients, normal human serum, CVF (cobra venom factor cobra venom factor: 1 mg/ml, from Comptech Company), anti human erythrocyte polyclonal antibody (from Rockland Company), Bio-Tek synergy HT multifunctional microplate reader (from Labsystems Company of Finland), Minispin table model high speed centrifuge (from Eppendorf of Germany), DK-8D Electro-Thermostatic Water Cabinet (from Shanghai Jinghong Experimental Equipment Co., Ltd.)

2. Experimental Method 2.1. CRIg-L-fH Inhibits Complement AP Induced Hemolysis of PNH Erythrocytes Samples of red blood cells (RBC) collected from seven PNH patients with terminal blood collection are washed three times by PBS (5000 rpm, centrifugation of 3 min), then prepare them into 4% RBC solution. To a 200 µl reaction system, add 4% RBC 25 µl (10% final concentration), and then add a diluted CRIg-L-fH protein solution to form a final 0-3 µM concentration gradient, CVF (100 µg/ml) 4 µl, normal human serum 20 µl (10% final concentration). Blank control and total lysis control are set up at the same time. At 37° C., after 30 min of water bath and 1 min of 10,000 rpm centrifugation, 100 µl of supernatant is taken and subject to the detection of absorbance at OD414 nm by microplate reader.

2.2. CRIg-L-fH Inhibits Complement CP Induced Hemolysis of PNH Erythrocytes

Samples of red blood cells (RBC) collected from seven PNH patients are washed three times by PBS (5000 rpm, centrifugation of 3 min), then prepare them into 4% RBC solution. To a 200 µl reaction system, add 4% RBC 25 µl (1% final concentration), and then add a diluted CRIg-L-fH protein solution to form a final 0-3 µM concentration gradient, anti-human RBC antibody (5 mg/ml) 2 µl, normal human serum 20 µl (10% final concentration). Blank control and total lysis control are set up at the same time. At 37° C., after 30 min of water bath and 1 min of 10,000 rpm centrifugation, 100 µl of supernatants is taken and subject to the detection of absorbance at OD414 nm by microplate reader.

2.3 Statistical Processing Method

Data is shown by standard deviation (mean±SD). The graph is constructed by Excel.

3. Experimental Results

Figure 4:
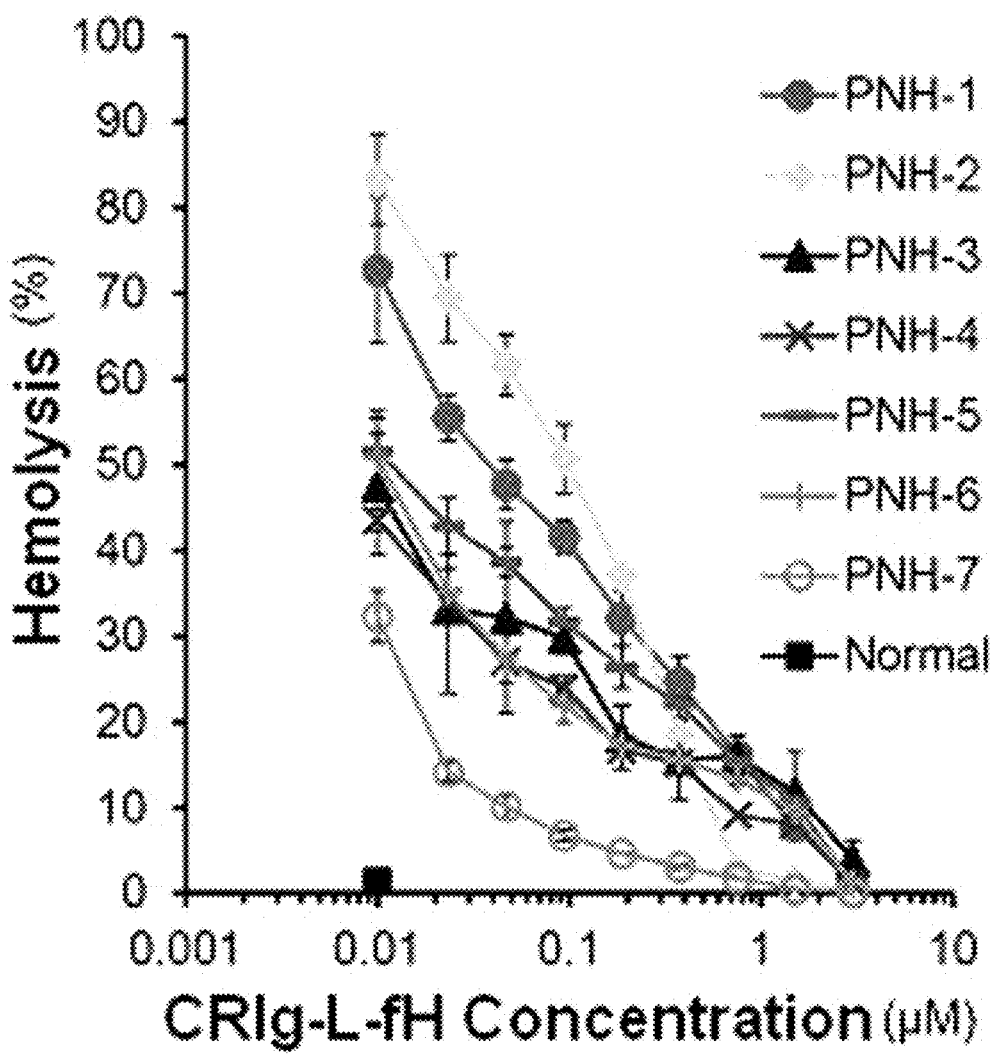
FIG. 4 is a schematic diagram of the protective effects of CRIg-L-fH from the hemolysis induced by complement alternative pathway of PNH patients' erythrocytes in seven cases.
Figure 5:
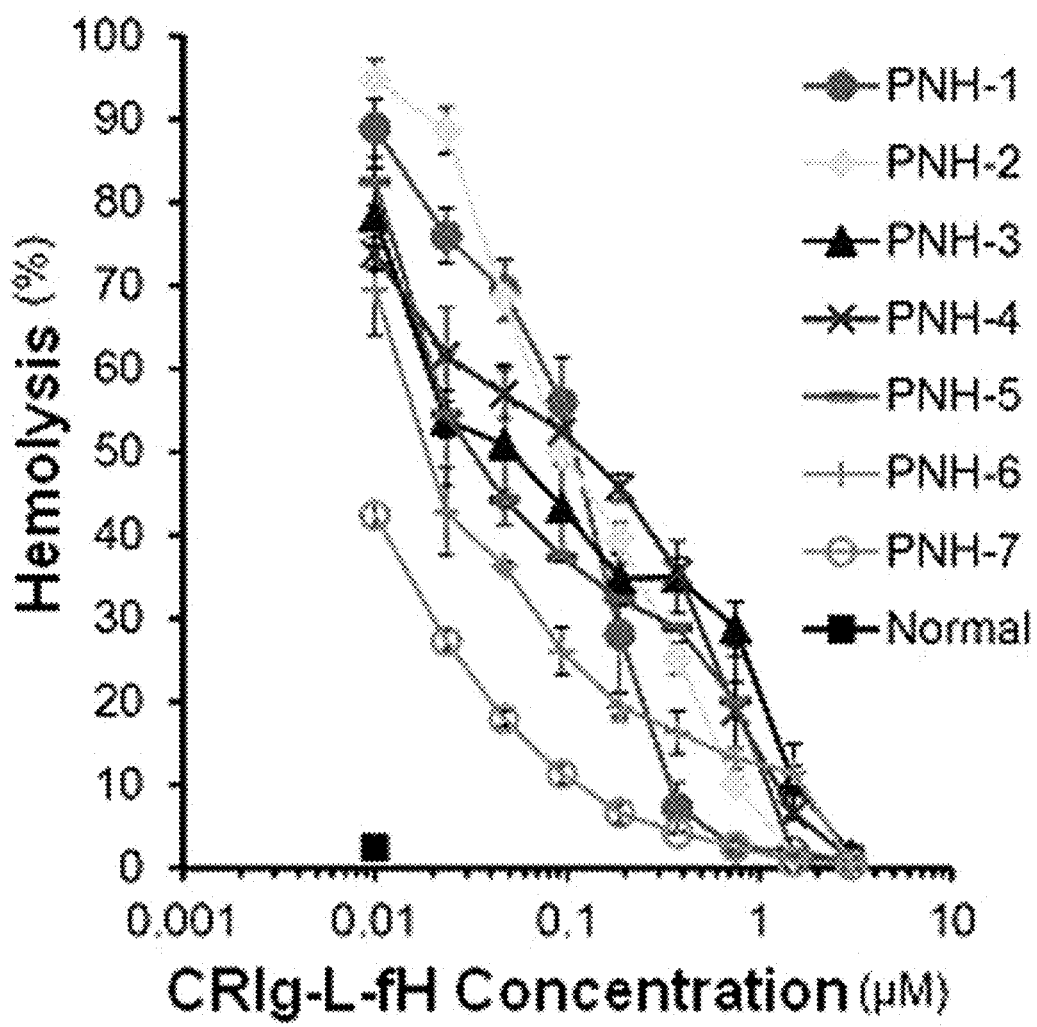
FIG. 5 is a schematic diagram of the protective effects of CRIg-L-fH from the hemolysis induced by complement classical pathway of PNH patients' erythrocytes in seven cases.
Figure 6:
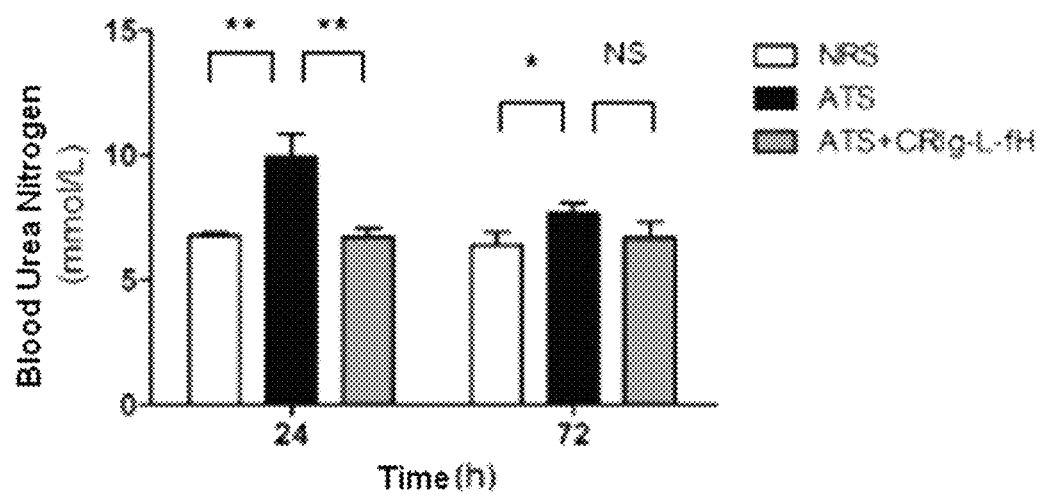
FIG. 6 is a schematic diagram of the relieving effect result of CRIg-L-fH to Thy-1N rat nephritis pathological symptoms of elevated serum urea nitrogen.
Figure 7:
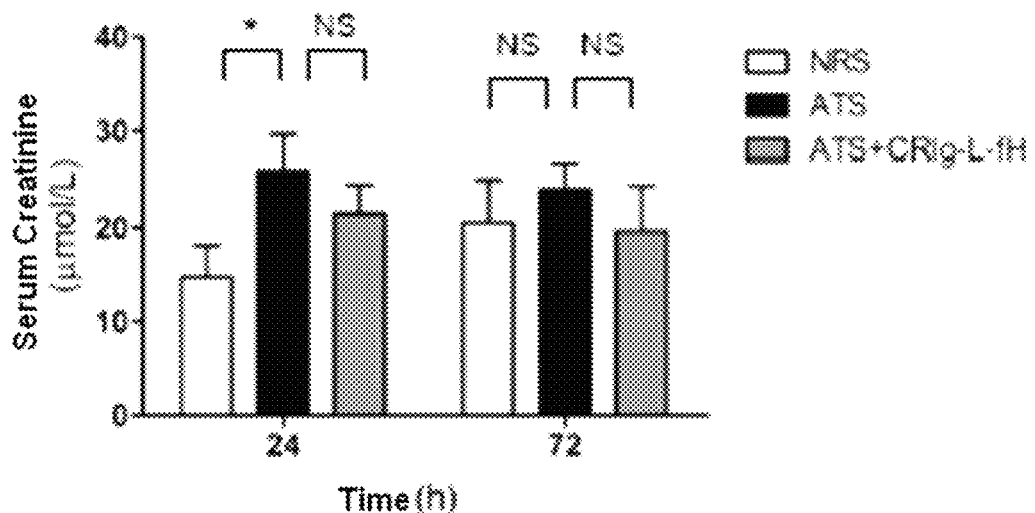
FIG. 7 is a schematic diagram of the relieving effect result of CRIg-L-fH to Thy-1N rat nephritis pathological symptoms of elevated serum creatinine.
Figure 8:
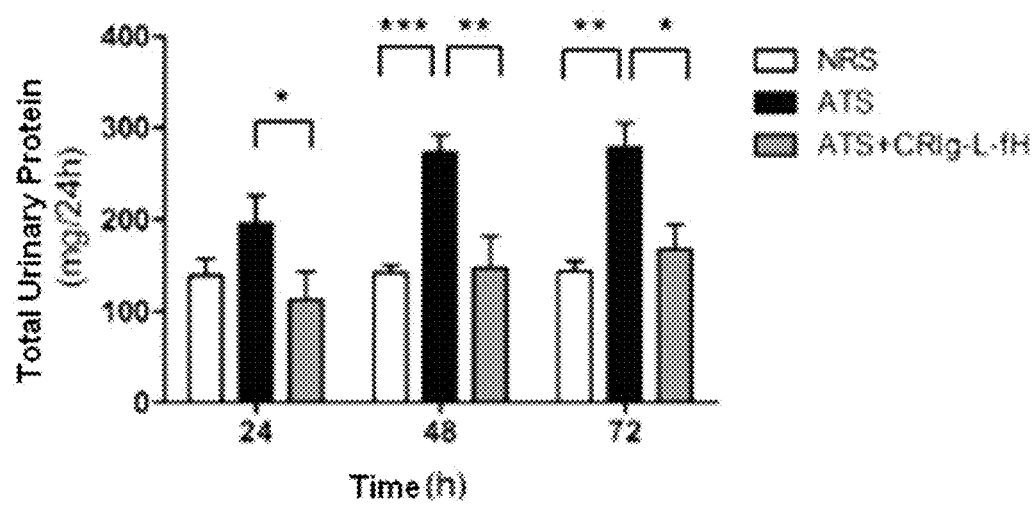
FIG. 8 is a schematic diagram of the relieving effect result of CRIg-L-fH to Thy-1N rat nephritis pathological symptoms of total protein leakage of urine.
Figure 9:
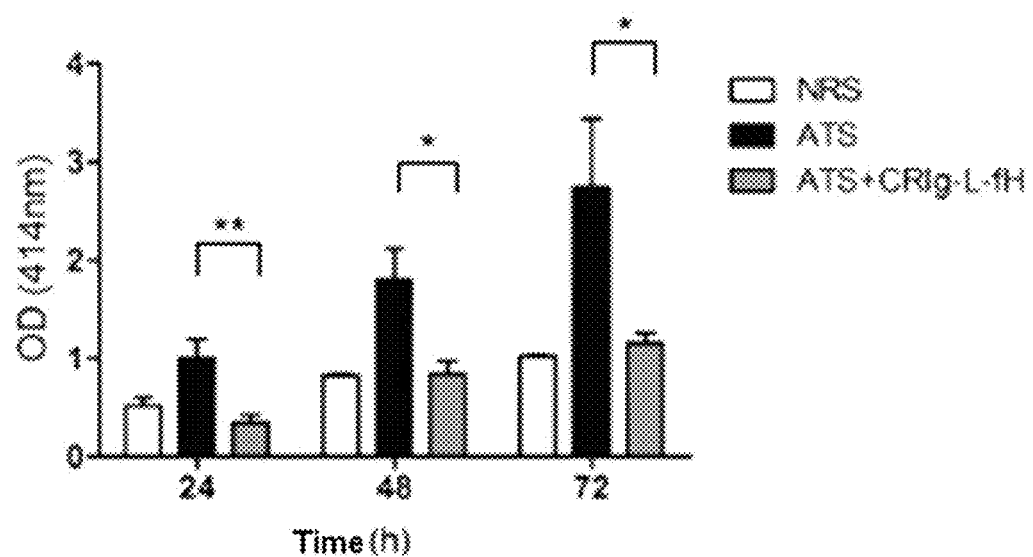
FIG. 9 is a schematic diagram of the relieving effect result of CRIg-L-fH Thy-1N rat nephritis pathological symptoms of hematuria.

The result of hemolysis experiment in vitro shows that CRIg-L-fH protein has a certain degree of inhibition to both complement AP and CP induced PNH erythrocytehemolysis, wherein the inhibition of complement AP is more prominent, as shown in FIG. 4 and FIG. 5.

Example 4: The Release Effect of CRIg-L-fH to Rat Thy-IN Nephritis

1. Instruments and Materials

Bio-Tek synergy HT multifunctional microplate reader (from Labsystems Company of Finland), FV500 laser confocal microscope (from Olympus Company of Japan), BCA protein quantitative reagent kit (from Thermo Fisher Company), Cobas 6000 analyzer fully automatic biochemical analyzer (from Roche Company), SD rat, anti-C3b/iC3b-FITC antibody, anti-SC5b-9 antibody, anti-His antibody, rabbit anti-mouse IgG-FITC antibody (rabbit anti-mouse)

2. Experimental Method 2.1 The Establishment of Rt Thy-1 Nephritis Model

Male SD rats are fed in the SPF (specific pathogen-free) level environment to 150-200 g body weight and divided into three groups in random for modeling.

(1) NRS group (n=4): rats are injected with normal rabbit serum (NRS) by tail-vein injection, the injection dosage is 1 ml/100 g body weight;

(2) ATS group (n=4): rats are injected with rabbit anti-rat thymocyte serum (ATS) by tail-vein injection, the injection dosage is 1 ml/100 g body weight.

(3) ATS+CRIg-L-fH group (n=4): rats are injected with rabbit anti-rat thymocyte serum (ATS) by tail-vein injection, the injection dosage is 1 ml/100 g body weight, then inject combining with the CRIg-L-fH by tail-vein injection, the injection dosage is 1 mg/100 g body weight.

2.2 Detection of the Index of Rat Nephritis

After injection, the rats are fed in the rat metabolic cage. After 24 hr and 72 hr of injection, blood samples are collected through the tail vein into standard coagulant tubes. After standing at room temperature for 30 min, the samples are centrifuged 3000 rpm for 10 min, the blood supernatants (serum) is taken and applied to detection and data collection of kidney function index (blood urea nitrogen or serum creatinine) by Cobas 6000 analyzer.

After 24 hr, 48 hr and 72 hr of injection, urine samples are collected with the rat metabolic cage. The urine sample is diluted to 50 times. BCA Protein Assay reagent kit measurement is applied to the test of the total protein concentration in urine, total protein (mg/24 hr)=BCA protein concentration ×50 (dilution ratio)×total volume of the urine. 100 µl of the diluted urine is added to 96 wells microtiter plate and the absorbance at OD414 nm is read directly from Bio-Tek microplate reader to measure the hemoglobin content in urine.

2.3 Immunofluorescence Detection of the Deposition of IgG C3 Fragment and CRIg-L-fH of Rat Kidney Frozen Sections After 3 and 7 days of injection, a rat is chosen from each group in random, after ether anaesthesia, the left ventricular is pinned for cardiac perfusion. Physiological saline is perfused first, when the liver is turned from red to white, perfuse 4% paraformaldehyde until the rat death. The left kidney is removed, and soaked in PBS, washed by rinse for several times, freezed in cell cryopreserved tubes with liquid nitrogen for 30 min, then stored under –80° C.

Open the freezing microtome, when the temperature reaches –20° C., the frozen kidney tissue is taken out from –80° C., embedded in the OCT. The surrounding tissue is cut by freezing microtome. The organization region located at the junction of renal cortex and medulla is selected and cut into 6 µm slices and attached on glass slide. The slices are fixed by 4% paraformaldehyde for 15 min, rinsed by PBS, blocked by 10% normal sheep serum, incubated with anti-C3b/iC3b, anti-His, anti-SC5b-9 antibody at 4 degrees overnight. On the next day, after washing by PBS for 3 times, the slices are incubated with secondary antibody, then rinsed by PBS, sealed and examined by microscopic.

3. Experimental Results

Figure 10:
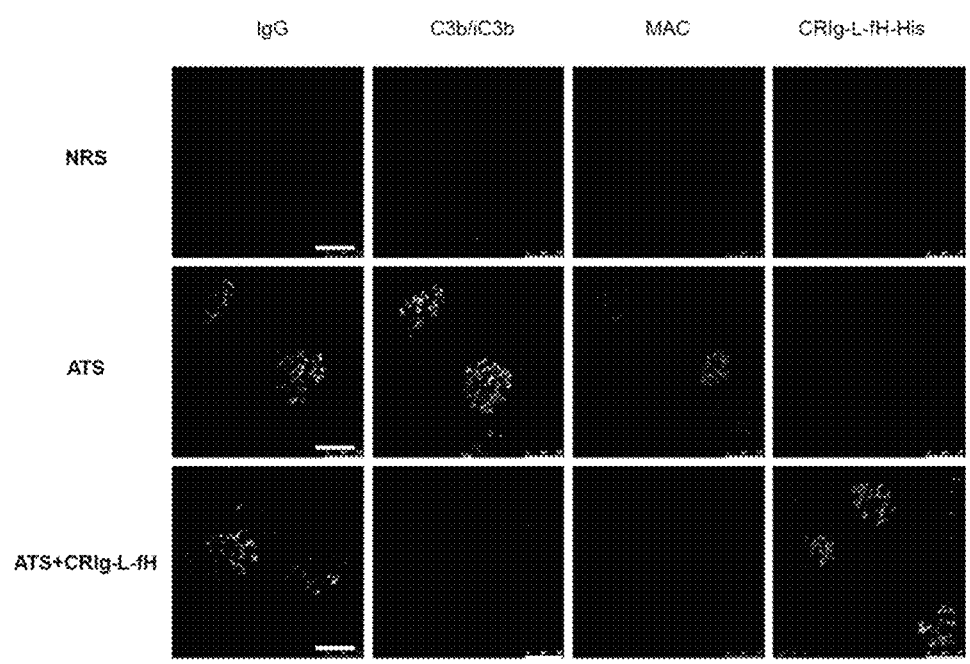
FIG. 10 is shown the deposition results of immunofluorescence detection of each group rat kidney cryosections of IgG, C3 fragment, MAC and CRIg-L-fH.

Comparation of the CRIg-L-fH treated Thy-IN rats with the untreated group shows that the content of blood urea nitrogen (BUN) and serum creatinine (Scr) are decreased, the levels of total protein and hemoglobin (HGB) in urine are reduced, a lot of CRIg-L-fH deposits in glomerular mesangial area (GMA) at the same time, and almost no C3b/iC3b deposition. These proves that CRIg-L-fH can mitigate the symptoms of rat Th-1N nephritis in a certain degree, as shown in FIG. 6-10 (FIG. 10: *P<0.05, P<0.01, *P<0.001; n=4).

In summary, the inhibitor targeting specific complement provided by the present invention is a novel target specific complement inhibitor, which can specifically target to the activation site of complement in vivo, and long-term inhibit complement activation and the cell and tissue damages mediated by complement activation. It can not only protect the human defective PNH erythrocytes from the hemolytic damage caused by complement attack, but also apparently relieve the mesangial proliferative lesions induced by complement in the Thy-1 nephritis rat model. Moreover, it indicates the inhibitor targeting specific complement can be effective in the treatment for other diseases of complement system over-activation, such as age related macular degeneration, atypical soluble hemorrhagic uremic syndrome, rheumatoid arthritis, ankylosing spondylitis, lupus erythematosus, and the like. Therefore, the inhibitor targeting specific complement provided by the present invention has great potential for medicinal application value and development prospects.

Despite the detailed introduction to the invention as above, the above introduction could not be considered as the limitation to the invention. After the person skilled in the art has read the above contents, the modifications and alternations of the invention will be obvious. Therefore, the protection scope of the invention shall be limited by the attached claims.

SEQUENCE LISTING

```
<160> NUMBER OF SEQ ID NOS: 12

<210> SEQ ID NO 1
<211> LENGTH: 1278
<212> TYPE: DNA
<213> ORGANISM: Artificial Sequence
<220> FEATURE:
<223> OTHER INFORMATION: CRIg-fH

<400> SEQUENCE: 1
atgggccgtc ccatcctgga agtgccagag agtgtaacag gaccttggaa aggggatgtg      60
aatcttccct gcacctatga cccctgcaa ggctacaccc aagtcttggt gaagtggctg     120
gtacaacgtg gctcagaccc tgtcaccatc tttctacgtg actcttctgg agaccatatc     180
cagcaggcaa agtaccaggg ccgcctgcat gtgagccaca aggttccagg agatgtatcc     240
ctccaattga gcaccctgga gatggatgac cggagccact acacgtgtga agtcacctgg     300
cagactcctg atggcaacca agtcgtgaga gataagatta ctgagctccg tgtccagaaa     360
gaagattgca atgaacttcc tccaagaaga aatacagaaa ttctgacagg ttcctggtct     420
```

-continued

```
gaccaaacat atccagaagg cacccaggct atctataaat gccgccctgg atatagatct    480
cttggaaatg taataatggt atgcaggaag ggagaatggg ttgctcttaa tccattaagg    540
aaatgtcaga aaaggccctg tggacatcct ggagatactc cttttggtac ttttacccct    600
acaggaggaa atgtgtttga atatggtgta aaagctgtgt atacatgtaa tgagggtat     660
caattgctag gtgagattaa ttaccgtgaa tgtgacacag atggatggac caatgatatt    720
cctatatgtg aagttgtgaa gtgtttacca gtgacagcac cagagaatgg aaaaattgtc    780
agtagtgcaa tggaaccaga tcgggaatac cattttggac aagcagtacg gtttgtatgt    840
aactcaggct acaagattga aggagatgaa gaaatgcatt gttcagacga tggttttttgg   900
agtaaagaga accaaagtg tgtggaaatt tcatgcaaat ccccagatgt tataaatgga     960
tctcctatat ctcagaagat tatttataag gagaatgaac gatttcaata taatgtaac    1020
atgggttatg aatacagtga agaggagat gctgtatgca ctgaatctgg atggcgtccg    1080
ttgccttcat gtgaagaaaa atcatgtgat aatccttata ttccaaatgg tgactactca    1140
cctttaagga ttaaacacag aactggagat gaaatcacgt accagtgtag aaatggtttt    1200
tatcctgcaa cccggggaaa tacagcaaaa tgcacaagta ctggctggat acctgctccg    1260
agatgtacct tgaaataa                                                  1278
```

<210> SEQ ID NO 2
<211> LENGTH: 425
<212> TYPE: PRT
<213> ORGANISM: Artificial Sequence
<220> FEATURE:
<223> OTHER INFORMATION: CRIg

<400> SEQUENCE: 2

Met Gly Arg Pro Ile Leu Glu Val Pro Glu Ser Val Thr Gly Pro Trp
1               5                   10                  15

Lys Gly Asp Val Asn Leu Pro Cys Thr Tyr Asp Pro Leu Gln Gly Tyr
                20                  25                  30

Thr Gln Val Leu Val Lys Trp Leu Val Gln Arg Gly Ser Asp Pro Val
            35                  40                  45

Thr Ile Phe Leu Arg Asp Ser Ser Gly Asp His Ile Gln Gln Ala Lys
        50                  55                  60

Tyr Gln Gly Arg Leu His Val Ser His Lys Val Pro Gly Asp Val Ser
65                  70                  75                  80

Leu Gln Leu Ser Thr Leu Glu Met Asp Asp Arg Ser His Tyr Thr Cys
                85                  90                  95

Glu Val Thr Trp Gln Thr Pro Asp Gly Asn Gln Val Val Arg Asp Lys
            100                 105                 110

Ile Thr Glu Leu Arg Val Gln Lys Glu Asp Cys Asn Glu Leu Pro Pro
        115                 120                 125

Arg Arg Asn Thr Glu Ile Leu Thr Gly Ser Trp Ser Asp Gln Thr Tyr
    130                 135                 140

Pro Glu Gly Thr Gln Ala Ile Tyr Lys Cys Arg Pro Gly Tyr Arg Ser
145                 150                 155                 160

Leu Gly Asn Val Ile Met Val Cys Arg Lys Gly Glu Trp Val Ala Leu
                165                 170                 175

Asn Pro Leu Arg Lys Cys Gln Lys Arg Pro Cys Gly His Pro Gly Asp
            180                 185                 190

Thr Pro Phe Gly Thr Phe Thr Leu Thr Gly Gly Asn Val Phe Glu Tyr
        195                 200                 205

-continued

```
Gly Val Lys Ala Val Tyr Thr Cys Asn Glu Gly Tyr Gln Leu Leu Gly
    210                 215                 220

Glu Ile Asn Tyr Arg Glu Cys Asp Thr Asp Gly Trp Thr Asn Asp Ile
225                 230                 235                 240
Pro Ile Cys Glu Val Val Lys Cys Leu Pro Val Thr Ala Pro Glu Asn
                245                 250                 255
Gly Lys Ile Val Ser Ser Ala Met Glu Pro Asp Arg Glu Tyr His Phe
            260                 265                 270

Gly Gln Ala Val Arg Phe Val Cys Asn Ser Gly Tyr Lys Ile Glu Gly
        275                 280                 285

Asp Glu Glu Met His Cys Ser Asp Asp Gly Phe Trp Ser Lys Glu Lys
    290                 295                 300

Pro Lys Cys Val Glu Ile Ser Cys Lys Ser Pro Asp Val Ile Asn Gly
305                 310                 315                 320
Ser Pro Ile Ser Gln Lys Ile Ile Tyr Lys Glu Asn Glu Arg Phe Gln
                325                 330                 335
Tyr Lys Cys Asn Met Gly Tyr Glu Tyr Ser Glu Arg Gly Asp Ala Val
            340                 345                 350

Cys Thr Glu Ser Gly Trp Arg Pro Leu Pro Ser Cys Glu Glu Lys Ser
        355                 360                 365

Cys Asp Asn Pro Tyr Ile Pro Asn Gly Asp Tyr Ser Pro Leu Arg Ile
    370                 375                 380

Lys His Arg Thr Gly Asp Glu Ile Thr Tyr Gln Cys Arg Asn Gly Phe
385                 390                 395                 400
Tyr Pro Ala Thr Arg Gly Asn Thr Ala Lys Cys Thr Ser Thr Gly Trp
                405                 410                 415
Ile Pro Ala Pro Arg Cys Thr Leu Lys
            420                 425

<210> SEQ ID NO 3
<211> LENGTH: 1323
<212> TYPE: DNA
<213> ORGANISM: Artificial Sequence
<220> FEATURE:
<223> OTHER INFORMATION: CRIg-(Gly4Ser)3-fH

<400> SEQUENCE: 3
atgggccgtc ccatcctgga agtgccagag agtgtaacag gaccttggaa aggggatgtg     60
aatcttccct gcacctatga ccccctgcaa ggctacaccc aagtcttggt gaagtggctg    120
gtacaacgtg gctcagaccc tgtcaccatc tttctacgtg actcttctgg agaccatatc    180
cagcaggcaa agtaccaggg ccgcctgcat gtgagccaca aggttccagg agatgtatcc    240
ctccaattga gcaccctgga gatggatgac cggagccact acacgtgtga agtcacctgg    300
cagactcctg atggcaacca agtcgtgaga gataagatta ctgagctccg tgtccagaaa    360
tctggtggcg gtggctccgg cggaggtggg tccggtggcg gcggagaaga ttgcaatgaa    420
cttcctccaa gaagaaatac agaaattctg acaggttcct ggtctgacca aacatatcca    480
gaaggcaccc aggctatcta taaatgccgc cctggatata gatctcttgg aaatgtaata    540
atggtatgca ggaagggaga atgggttgct cttaatccat taaggaaatg tcagaaaagg    600
ccctgtggac atcctggaga tactcctttt ggtactttta cccttacagg aggaaatgtg    660
tttgaatatg gtgtaaaagc tgtgtataca tgtaatgagg ggtatcaatt gctaggtgag    720
attaattacc gtgaatgtga cacagatgga tggaccaatg atattcctat atgtgaagtt    780
gtgaagtgtt taccagtgac agcaccagag aatggaaaaa ttgtcagtag tgcaatggaa    840
```

-continued

```
ccagatcggg aataccattt tggacaagca gtacggtttg tatgtaactc aggctacaag      900
attgaaggag atgaagaaat gcattgttca gacgatggtt tttggagtaa agagaaacca      960
aagtgtgtgg aaatttcatg caaatcccca gatgttataa atggatctcc tatatctcag     1020
aagattattt ataaggagaa tgaacgattt caatataaat gtaacatggg ttatgaatac     1080
agtgaaagag gagatgctgt atgcactgaa tctggatggc gtccgttgcc ttcatgtgaa     1140
gaaaaatcat gtgataatcc ttatattcca aatggtgact actcaccttt aaggattaaa     1200
cacagaactg gagatgaaat cacgtaccag tgtagaaatg ttttttatcc tgcaacccgg     1260
ggaaatacag caaaatgcac aagtactggc tggatacctg ctccgagatg taccttgaaa     1320
taa                                                                   1323
```

<210> SEQ ID NO 4
<211> LENGTH: 440
<212> TYPE: PRT
<213> ORGANISM: Artificial Sequence
<220> FEATURE:
<223> OTHER INFORMATION: factor H

<400> SEQUENCE: 4

```
Met Gly Arg Pro Ile Leu Glu Val Pro Glu Ser Val Thr Gly Pro Trp
  1               5                  10                  15

Lys Gly Asp Val Asn Leu Pro Cys Thr Tyr Asp Pro Leu Gln Gly Tyr
                 20                  25                  30

Thr Gln Val Leu Val Lys Trp Leu Val Gln Arg Gly Ser Asp Pro Val
             35                  40                  45

Thr Ile Phe Leu Arg Asp Ser Ser Gly Asp His Ile Gln Gln Ala Lys
         50                  55                  60

Tyr Gln Gly Arg Leu His Val Ser His Lys Val Pro Gly Asp Val Ser
 65                  70                  75                  80

Leu Gln Leu Ser Thr Leu Glu Met Asp Asp Arg Ser His Tyr Thr Cys
                 85                  90                  95

Glu Val Thr Trp Gln Thr Pro Asp Gly Asn Gln Val Val Arg Asp Lys
            100                 105                 110

Ile Thr Glu Leu Arg Val Gln Lys Ser Gly Gly Gly Ser Gly Gly
        115                 120                 125

Gly Gly Ser Gly Gly Gly Gly Glu Asp Cys Asn Glu Leu Pro Pro Arg
    130                 135                 140

Arg Asn Thr Glu Ile Leu Thr Gly Ser Trp Ser Asp Gln Thr Tyr Pro
145                 150                 155                 160

Glu Gly Thr Gln Ala Ile Tyr Lys Cys Arg Pro Gly Tyr Arg Ser Leu
                165                 170                 175

Gly Asn Val Ile Met Val Cys Arg Lys Gly Glu Trp Val Ala Leu Asn
            180                 185                 190

Pro Leu Arg Lys Cys Gln Lys Arg Pro Cys Gly His Pro Gly Asp Thr
        195                 200                 205

Pro Phe Gly Thr Phe Thr Leu Thr Gly Gly Asn Val Phe Glu Tyr Gly
    210                 215                 220

Val Lys Ala Val Tyr Thr Cys Asn Glu Gly Tyr Gln Leu Leu Gly Glu
225                 230                 235                 240

Ile Asn Tyr Arg Glu Cys Asp Thr Asp Gly Trp Thr Asn Asp Ile Pro
                245                 250                 255

Ile Cys Glu Val Val Lys Cys Leu Pro Val Thr Ala Pro Glu Asn Gly
            260                 265                 270
```

```
Lys Ile Val Ser Ser Ala Met Glu Pro Asp Arg Glu Tyr His Phe Gly
            275                 280                 285

Gln Ala Val Arg Phe Val Cys Asn Ser Gly Tyr Lys Ile Glu Gly Asp
        290                 295                 300

Glu Glu Met His Cys Ser Asp Asp Gly Phe Trp Ser Lys Glu Lys Pro
305                 310                 315                 320

Lys Cys Val Glu Ile Ser Cys Lys Ser Pro Asp Val Ile Asn Gly Ser
                325                 330                 335

Pro Ile Ser Gln Lys Ile Ile Tyr Lys Glu Asn Glu Arg Phe Gln Tyr
            340                 345                 350

Lys Cys Asn Met Gly Tyr Glu Tyr Ser Glu Arg Gly Asp Ala Val Cys
        355                 360                 365

Thr Glu Ser Gly Trp Arg Pro Leu Pro Ser Cys Glu Glu Lys Ser Cys
370                 375                 380

Asp Asn Pro Tyr Ile Pro Asn Gly Asp Tyr Ser Pro Leu Arg Ile Lys
385                 390                 395                 400

His Arg Thr Gly Asp Glu Ile Thr Tyr Gln Cys Arg Asn Gly Phe Tyr
                405                 410                 415

Pro Ala Thr Arg Gly Asn Thr Ala Lys Cys Thr Ser Thr Gly Trp Ile
            420                 425                 430

Pro Ala Pro Arg Cys Thr Leu Lys
        435                 440

<210> SEQ ID NO 5
<211> LENGTH: 1200
<212> TYPE: DNA
<213> ORGANISM: Artificial Sequence
<220> FEATURE:
<223> OTHER INFORMATION: CRIg

<400> SEQUENCE: 5
atggggatct tactgggcct gctactcctg gggcacctaa cagtggacac ttatggccgt      60
cccatcctgg aagtgccaga gagtgtaaca ggaccttgga aggggatgt gaatcttccc     120 tgcacctatg accccctgca aggctacacc caagtcttgg tgaagtggct ggtacaacgt     180
ggctcagacc ctgtcaccat cttctacgt gactcttctg agaccatat ccagcaggca      240 aagtaccagg gccgcctgca gtgagccac aaggttccag agatgtatc cctccaattg      300 agcaccctgg agatggatga ccggagccac tacacgtgtg aagtcacctg gcagactcct     360
gatggcaacc aagtcgtgag agataagatt actgagctcc gtgtccagaa actctctgtc     420
tccaagccca cagtgacaac tggcagcggt tatggcttca cggtgcccca gggaatgagg     480
attagccttc aatgccaggc tcggggttct cctcccatca gttatatttg gtataagcaa     540
cagactaata accaggaacc catcaaagta gcaaccctaa gtaccttact cttcaagcct     600
gcggtgatag ccgactcagg ctcctatttc tgcactgcca agggccaggt tggctctgag     660
cagcacagcg acattgtgaa gtttgtggtc aaagactcct caaagctact caagaccaag     720
actgaggcac ctacaaccat gacataccc ttgaaagcaa catctacagt gaagcagtcc      780
tgggactgga ccactgacat ggatggctac cttggagaga ccagtgctgg gccaggaaag     840
agcctgcctg tctttgccat catcctcatc atctccttgt gctgtatggt ggttttacc      900 atggcctata tcatgctctg tcggaagaca tcccaacaag agcatgtcta cgaagcagcc     960
agggcacatg ccagagaggc caacgactct ggagaaacca tgagggtggc catcttcgca    1020
agtggctgct ccagtgatga gccaacttcc cagaatctgg caacaactac tctgatgag     1080
```

```
cccctgcatag gacaggagta ccagatcatc gcccagatca atggcaacta cgccgcctg    1140 ctggacacag ttcctctgga ttatgagttt ctggccactg agggcaaaag tgtctgttaa    1200
```

<210> SEQ ID NO 6
<211> LENGTH: 399
<212> TYPE: PRT
<213> ORGANISM: Artificial Sequence
<220> FEATURE:
<223> OTHER INFORMATION: CRIg

<400> SEQUENCE: 6

```
Met Gly Ile Leu Leu Gly Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys Leu Ser Val Ser Lys Pro Thr
    130                 135                 140

Val Thr Thr Gly Ser Gly Tyr Gly Phe Thr Val Pro Gln Gly Met Arg
145                 150                 155                 160

Ile Ser Leu Gln Cys Gln Ala Arg Gly Ser Pro Pro Ile Ser Tyr Ile
                165                 170                 175

Trp Tyr Lys Gln Gln Thr Asn Asn Gln Glu Pro Ile Lys Val Ala Thr
            180                 185                 190

Leu Ser Thr Leu Leu Phe Lys Pro Ala Val Ile Ala Asp Ser Gly Ser
        195                 200                 205

Tyr Phe Cys Thr Ala Lys Gly Gln Val Gly Ser Glu Gln His Ser Asp
    210                 215                 220

Ile Val Lys Phe Val Val Lys Asp Ser Ser Lys Leu Leu Lys Thr Lys
225                 230                 235                 240

Thr Glu Ala Pro Thr Thr Met Thr Tyr Pro Leu Lys Ala Thr Ser Thr
                245                 250                 255

Val Lys Gln Ser Trp Asp Trp Thr Thr Asp Met Asp Gly Tyr Leu Gly
            260                 265                 270

Glu Thr Ser Ala Gly Pro Gly Lys Ser Leu Pro Val Phe Ala Ile Ile
        275                 280                 285

Leu Ile Ile Ser Leu Cys Cys Met Val Val Phe Thr Met Ala Tyr Ile
    290                 295                 300

Met Leu Cys Arg Lys Thr Ser Gln Gln Glu His Val Tyr Glu Ala Ala
305                 310                 315                 320

Arg Ala His Ala Arg Glu Ala Asn Asp Ser Gly Glu Thr Met Arg Val
                325                 330                 335

Ala Ile Phe Ala Ser Gly Cys Ser Ser Asp Glu Pro Thr Ser Gln Asn
```

```
                340             345              350
Leu Gly Asn Asn Tyr Ser Asp Glu Pro Cys Ile Gly Gln Glu Tyr Gln
         355                  360                  365

Ile Ile Ala Gln Ile Asn Gly Asn Tyr Ala Arg Leu Leu Asp Thr Val
    370                 375                 380

Pro Leu Asp Tyr Glu Phe Leu Ala Thr Glu Gly Lys Ser Val Cys
385                 390                 395

<210> SEQ ID NO 7
<211> LENGTH: 3696
<212> TYPE: DNA
<213> ORGANISM: Artificial Sequence
<220> FEATURE:
<223> OTHER INFORMATION: factor H

<400> SEQUENCE: 7
atgagacttc tagcaaagat tatttgcctt atgttatggg ctatttgtgt agcagaagat      60
tgcaatgaac ttcctccaag aagaaataca gaaattctga caggttcctg gtctgaccaa    120
acatatccag aaggcaccca ggctatctat aaatgccgcc ctggatatag atctcttgga    180
aatgtaataa tggtatgcag aagggagaa tgggttgctc ttaatccatt aaggaaatgt    240
cagaaaaggc cctgtggaca tcctggagat actccttttg gtacttttac ccttacagga    300
ggaaatgtgt ttgaatatgg tgtaaaagct gtgtatacat gtaatgaggg gtatcaattg    360
ctaggtgaga ttaattaccg tgaatgtgac acagatggat ggaccaatga tattcctata    420
tgtgaagttg tgaagtgttt accagtgaca gcaccagaga tggaaaaaat tgtcagtagt    480
gcaatggaac cagatcggga ataccatttt ggacaagcag tacggtttgt atgtaactca    540
ggctacaaga ttgaaggaga tgaagaaatg cattgttcag cgatggttt tggagtaaa    600 gagaaaccaa gtgtgtgga atttcatgc aaatccccag atgttataaa tggatctcct    660
atatctcaga gattattta taaggagaat gaacgatttc aatataaatg taacatgggt    720
tatgaataca gtgaaagagg agatgctgta tgcactgaat ctggatggcg tccgttgcct    780
tcatgtgaag aaaaatcatg tgataatcct tatattccaa atggtgacta ctcacccttta    840 aggattaaac acagaactgg agatgaaatc acgtaccagt gtagaaatgg ttttatcct    900 gcaacccggg gaaatacagc aaaatgcaca agtactggct ggataccctgc tccgagatgt    960 accttgaaac cttgtgatta tccagacatt aaacatggag gtctatatca tgagaatatg    1020
cgtagaccat actttccagt agctgtagga aaatattact cctattactg tgatgaacat    1080
tttgagactc cgtcaggaag ttactgggat cacattcatt gcacacaaga tggatggtcg    1140
ccagcagtac catgcctcag aaaatgttat tttccttatt tggaaaatgg atataatcaa    1200
aatcatggaa gaaagtttgt acagggtaaa tctatagacg ttgcctgcca tcctggctac    1260
gctcttccaa aagcgcagac cacagttaca tgtatggaga tggctggtc tcctactccc    1320 agatgcatcc gtgtcaaaac atgttccaaa tcaagtatag atattgagaa tgggtttatt    1380
tctgaatctc agtatacata tgccttaaaa gaaaaagcga atatcaatg caaactagga    1440 tatgtaacag cagatggtga aacatcagga tcaattacat gtgggaaaga tggatggtca    1500
gctcaaccca cgtgcattaa atcttgtgat atcccagtat ttatgaatgc cagaactaaa    1560
aatgacttca catggtttaa gctgaatgac acattggact atgaatgcca tgatggttat    1620
gaaagcaata ctggaagcac cactggtccc atagtgtgtg gttacaatgg ttggtctgat    1680
ttacccatat gttatgaaag agaatgcgaa cttcctaaaa tagatgtaca cttagttcct    1740
```

```
gatcgcaaga aagaccagta taaagttgga gaggtgttga aattctcctg caaaccagga    1800
tttacaatag ttggacctaa ttccgttcag tgctaccact ttggattgtc tcctgacctc    1860
ccaatatgta aagagcaagt acaatcatgt ggtccacctc ctgaactcct caatgggaat    1920
gttaaggaaa aaacgaaaga agaatatgga cacagtgaag tggtggaata ttattgcaat    1980
cctagatttc taatgaaggg acctaataaa attcaatgtg ttgatggaga gtggacaact    2040
ttaccagtgt gtattgtgga ggagagtacc tgtggagata tacctgaact tgaacatggc    2100
tgggcccagc tttcttcccc tccttattac tatggagatt cagtggaatt caattgctca    2160
gaatcattta caatgattgg acacagatca attacgtgta ttcatggagt atggacccaa    2220
cttccccagt gtgtggcaat agataaactt aagaagtgca aatcatcaaa tttaattata    2280
cttgaggaac atttaaaaaa caagaaggaa ttcgatcata attctaacat aaggtacaga    2340
tgtagaggaa aagaaggatg gatacacaca gtctgcataa atggaagatg ggatccagaa    2400
gtgaactgct caatggcaca aatacaatta tgcccacctc cacctcagat tcccaattct    2460
cacaatatga caaccacact gaattatcgg gatggagaaa agtatctgt tctttgccaa    2520 gaaaattatc taattcagga aggagaagaa attacatgca aagatggaag atggcagtca    2580
ataccactct gtgttgaaaa aattccatgt tcacaaccac ctcagataga acacggaacc    2640
attaattcat ccaggtcttc acaagaaagt tatgcacatg ggactaaatt gagttatact    2700
tgtgagggtg gtttcaggat atctgaagaa atgaaacaa catgctacat gggaaaatgg    2760
agttctccac ctcagtgtga aggccttcct tgtaaatctc cacctgagat ttctcatggt    2820
gttgtagctc acatgtcaga cagttatcag tatggagaag aagttacgta caaatgtttt    2880
gaaggttttg gaattgatgg gcctgcaatt gcaaaatgct taggagaaaa atggtctcac    2940
cctccatcat gcataaaaac agattgtctc agtttaccta gctttgaaaa tgccataccc    3000
atgggagaga agaaggatgt gtataaggcg ggtgagcaag tgacttacac ttgtgcaaca    3060
tattacaaaa tggatggagc cagtaatgta acatgcatta atagcagatg gacaggaagg    3120
ccaacatgca gagacacctc ctgtgtgaat ccgcccacag tacaaaatgc ttatatagtg    3180
tcgagacaga tgagtaaata tccatctggt gagagagtac gttatcaatg taggagccct    3240
tatgaaatgt ttgggatga agaagtgatg tgtttaaatg gaaactggac ggaaccacct    3300
caatgcaaag attctacagg aaaatgtggg ccccctccac ctattgacaa tgggacatt    3360 acttcattcc cgttgtcagt atatgctcca gcttcatcag ttgagtacca atgccagaac    3420
ttgtatcaac ttgagggtaa caagcgaata acatgtagaa atggacaatg gtcagaacca    3480
ccaaaatgct tacatccgtg tgtaatatcc cgagaaatta tggaaaatta acatagca    3540 ttaaggtgga cagccaaaca gaagctttat tcgagaacag gtgaatcagt tgaatttgtg    3600
tgtaaacggg gatatcgtct ttcatcacgt tctcacacat tgcgaacaac atgttgggat    3660
gggaaactgg agtatccaac ttgtgcaaaa agatag                               3696
```

<210> SEQ ID NO 8
<211> LENGTH: 1231
<212> TYPE: PRT
<213> ORGANISM: Artificial Sequence
<220> FEATURE:
<223> OTHER INFORMATION: factor H

<400> SEQUENCE: 8

```
Met Arg Leu Leu Ala Lys Ile Ile Cys Leu Met Leu Trp Ala Ile Cys
1               5                   10                  15
```

-continued

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn His Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys

```
                435                 440                 445
Ser Lys Ser Ser Ile Asp Ile Glu Asn Gly Phe Ile Ser Glu Ser Gln
450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
                500                 505                 510

Val Phe Met Asn Ala Arg Thr Lys Asn Asp Phe Thr Trp Phe Lys Leu
            515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
                580                 585                 590

Leu Lys Phe Ser Cys Lys Pro Gly Phe Thr Ile Val Gly Pro Asn Ser
            595                 600                 605

Val Gln Cys Tyr His Phe Gly Leu Ser Pro Asp Leu Pro Ile Cys Lys
            610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
                660                 665                 670

Cys Val Asp Gly Glu Trp Thr Thr Leu Pro Val Cys Ile Val Glu Glu
                675                 680                 685

Ser Thr Cys Gly Asp Ile Pro Glu Leu Glu His Gly Trp Ala Gln Leu
690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
            770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
850                 855                 860
```

```
Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 9
<211> LENGTH: 357
<212> TYPE: DNA
<213> ORGANISM: Artificial Sequence
<220> FEATURE:
```

<223> OTHER INFORMATION: CRIg extracellular domain

<400> SEQUENCE: 9

| | | |
|---|---|---|
| ggccgtccca tcctggaagt gccagagagt gtaacaggac cttggaaagg ggatgtgaat | 60 | |
| cttccctgca cctatgaccc cctgcaaggc tacacccaag tcttggtgaa gtggctggta | 120 | |
| caacgtggct cagaccctgt caccatcttt ctacgtgact cttctggaga ccatatccag | 180 | |
| caggcaaagt accagggccg cctgcatgtg agccacaagg ttccaggaga tgtatccctc | 240 | |
| caattgagca ccctggagat ggatgaccgg agccactaca cgtgtgaagt cacctggcag | 300 | |
| actcctgatg gcaaccaagt cgtgagagat aagattactg agctccgtgt ccagaaa | 357 | |

<210> SEQ ID NO 10
<211> LENGTH: 119
<212> TYPE: PRT
<213> ORGANISM: Artificial Sequence
<220> FEATURE:
<223> OTHER INFORMATION: Protein sequence (119aa)

<400> SEQUENCE: 10

Gly Arg Pro Ile Leu Glu Val Pro Glu Ser Val Thr Gly Pro Trp Lys
1               5                   10                  15

Gly Asp Val Asn Leu Pro Cys Thr Tyr Asp Pro Leu Gln Gly Tyr Thr
            20                  25                  30

Gln Val Leu Val Lys Trp Leu Val Gln Arg Gly Ser Asp Pro Val Thr
        35                  40                  45

Ile Phe Leu Arg Asp Ser Ser Gly Asp His Ile Gln Gln Ala Lys Tyr
    50                  55                  60

Gln Gly Arg Leu His Val Ser His Lys Val Pro Gly Asp Val Ser Leu
65                  70                  75                  80

Gln Leu Ser Thr Leu Glu Met Asp Asp Arg Ser His Tyr Thr Cys Glu
                85                  90                  95

Val Thr Trp Gln Thr Pro Asp Gly Asn Gln Val Val Arg Asp Lys Ile
            100                 105                 110

Thr Glu Leu Arg Val Gln Lys
        115

<210> SEQ ID NO 11
<211> LENGTH: 915
<212> TYPE: DNA
<213> ORGANISM: Artificial Sequence
<220> FEATURE:
<223> OTHER INFORMATION: Factor H SCR1-5 domain

<400> SEQUENCE: 11

| | | |
|---|---|---|
| gaagattgca atgaacttcc tccaagaaga aatacagaaa ttctgacagg ttcctggtct | 60 | |
| gaccaaacat atccagaagg cacccaggct atctataaat gccgccctgg atatagatct | 120 | |
| cttggaaatg taataatggt atgcaggaag ggagaatggg ttgctcttaa tccattaagg | 180 | |
| aaatgtcaga aaaggccctg tggacatcct ggagatactc cttttggtac ttttaccctt | 240 | |
| acaggaggaa atgtgtttga atatggtgta aaagctgtgt atacatgtaa tgagggtat | 300 | |
| caattgctag gtgagattaa ttaccgtgaa tgtgacacag atggatggac caatgatatt | 360 | |
| cctatatgtg aagttgtgaa gtgtttacca gtgacagcac cagagaatgg aaaaattgtc | 420 | |
| agtagtgcaa tggaaccaga tcgggaatac catttggac aagcagtacg gtttgtatgt | 480 | |
| aactcaggct acaagattga aggagatgaa gaaatgcatt gttcagacga tggttttggg | 540 | |
| agtaaagaga accaaagtg tgtggaaatt tcatgcaaat ccccagatgt tataaatgga | 600 | |

```
tctcctatat ctcagaagat tatttataag gagaatgaac gatttcaata taaatgtaac    660
atgggttatg aatacagtga aagaggagat gctgtatgca ctgaatctgg atggcgtccg    720
ttgccttcat gtgaagaaaa atcatgtgat aatccttata ttccaaatgg tgactactca    780
cctttaagga ttaaacacag aactggagat gaaatcacgt accagtgtag aaatggtttt    840
tatcctgcaa cccggggaaa tacagcaaaa tgcacaagta ctggctggat acctgctccg    900
agatgtacct tgaaa                                                    915

<210> SEQ ID NO 12
<211> LENGTH: 305
<212> TYPE: PRT
<213> ORGANISM: Artificial Sequence
<220> FEATURE:
<223> OTHER INFORMATION: Protein sequence (305aa)

<400> SEQUENCE: 12
```

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Val Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

-continued

```
Ala Lys Cys Thr Ser Thr Gly Trp Ile Pro Ala Pro Arg Cys Thr Leu
    290                 295                 300
Lys
305
```

The invention claimed is:

1. An inhibitor protein targeting specific complement comprising an amino acid sequence selected from the group consisting of SEQ ID NO. 2 and SEQ ID NO. 4, and having a targeted inhibition function against complement activation, comprising:
  - a CRIg extracellular domain amino acid sequence portion; and
  - a complement inhibiting domain amino acid sequence portion connected to the CRIg extracellular domain amino acid sequence portion, comprising at least a portion of factor H.

2. A nucleic acid which encodes the inhibitor protein targeting specific complement of claim 1.

3. The nucleic acid according to claim 2, contained within a vector.

4. The inhibitor according to claim 1, wherein the CRIg extracellular domain amino acid sequence is directly connected to the complement inhibiting domain amino acid sequence.

5. The inhibitor according to claim 1, wherein the CRIg extracellular domain amino acid sequence is connected to the complement inhibiting domain amino acid sequence through a linker amino acid sequence.

6. The nucleic acid according to claim 2, comprising a sequence selected from the group consisting of SEQ ID NO 1 and SEQ ID NO 3.

7. The nucleic acid according to claim 6, contained within a vector.

8. A method for preparing an inhibitor protein targeting specific complement, comprising:
  - connecting a nucleic acid sequence encoding a CRIg extracellular domain to a nucleic acid sequence encoding a complement inhibiting domain comprising at least a portion of Factor H, by gene splicing overlap extension PCR, to form a fusion sequence for an inhibitor protein targeting specific complement comprising an amino acid sequence selected from the group consisting of SEQ ID NO. 2 and SEQ ID NO. 4;
  - inserting the fusion sequence into an eukaryotic expression vector; and
  - inducing protein expression of the inhibitor protein targeting specific complement through an eukaryotic protein expression vector, the inhibitor protein targeting specific complement comprising the CRIg extracellular domain amino acid sequence portion and the complement inhibiting domain amino acid sequence portion connected to the CRIg extracellular domain amino acid sequence portion.

9. The method according to claim 8, further comprising purifying the expressed inhibitor protein targeting specific complement.

10. The method according to claim 8, further comprising the step of administering the inhibitor protein targeting specific complement to a mammal in a pharmaceutically acceptable formulation.

11. A method for treating a condition in a mammal associated with complement activation, comprising administering to the mammal an inhibitor protein targeting specific complement, having a targeted inhibition function against complement activation, comprising an amino acid sequence selected from the group consisting of SEQ ID NO. 2 and SEQ ID NO. 4, comprising:
  - a CRIg extracellular domain amino acid sequence portion; and
  - a complement inhibiting domain amino acid sequence portion comprising at least a portion of factor H, connected to the CRIg extracellular domain amino acid sequence portion.

12. The method according to claim 11, wherein the condition comprises paroxysmal nocturnal hemoglobinuria.

13. The method according to claim 11, further comprising administering a pharmaceutically acceptable formulation comprising the inhibitor protein targeting specific complement to a mammal.

14. The inhibitor protein targeting specific complement according to claim 1, wherein the amino acid sequence comprises SEQ ID NO. 2.

15. The inhibitor protein targeting specific complement according to claim 1, wherein the amino acid sequence comprises SEQ ID NO. 4.

16. The method according to claim 8, wherein the amino acid sequence comprises SEQ ID NO. 2.

17. The method according to claim 8, wherein the amino acid sequence comprises SEQ ID NO. 4.

18. The method according to claim 11, wherein the amino acid sequence comprises SEQ ID NO. 2.

19. The method according to claim 11, wherein the amino acid sequence comprises SEQ ID NO. 4.

* * * * *